United States Patent [19]

Bang et al.

[11] Patent Number: 4,992,373

[45] Date of Patent: * Feb. 12, 1991

[54] VECTORS AND COMPOUNDS FOR DIRECT EXPRESSION OF ACTIVATED HUMAN PROTEIN C

[75] Inventors: Nils U. Bang; Hartmut Ehrlich; Brian W. Grinnell; S. Richard Jaskunas, all of Indianapolis, Ind.

[73] Assignee: Eli Lilly and Company, Indianapolis, Ind.

[ * ] Notice: The portion of the term of this patent subsequent to Oct. 4, 2005 has been disclaimed.

[21] Appl. No.: 129,027

[22] Filed: Dec. 4, 1987

[51] Int. Cl.$^5$ .................... C12N 9/64; C12N 15/57; C12N 15/85; C12N 15/79

[52] U.S. Cl. ................. 435/226; 435/172.3; 435/240.1; 435/240.2; 435/254; 435/320.1; 536/27

[58] Field of Search .............. 435/68, 172.3, 240.23, 435/226, 320, 7; 536/27; 935/14, 32, 71, 81

[56] References Cited

U.S. PATENT DOCUMENTS

| | | | |
|---|---|---|---|
| 4,603,105 | 7/1986 | Kaplan | 435/7 |
| 4,696,895 | 9/1987 | Yamashita et al. | 435/7 |
| 4,769,326 | 9/1988 | Rutter | 435/68 |
| 4,775,624 | 10/1988 | Bang et al. | 435/226 |

Primary Examiner—Richard A. Schwartz
Assistant Examiner—Richard M. Lebovitz
Attorney, Agent, or Firm—Douglas K. Norman; Leroy Whitaker

[57] ABSTRACT

A method for the direct recombinant production of activated protein C is described. DNA compounds, vectors, and transformants useful in the method are also disclosed. The method involves transformation and culture of a host cell with a recombinant DNA vector that encodes a protein C molecule in which the activation peptide is replaced with a cleavage sequence for a cell associated protease.

17 Claims, 5 Drawing Sheets

The Construction of Plasmid pBKneo1

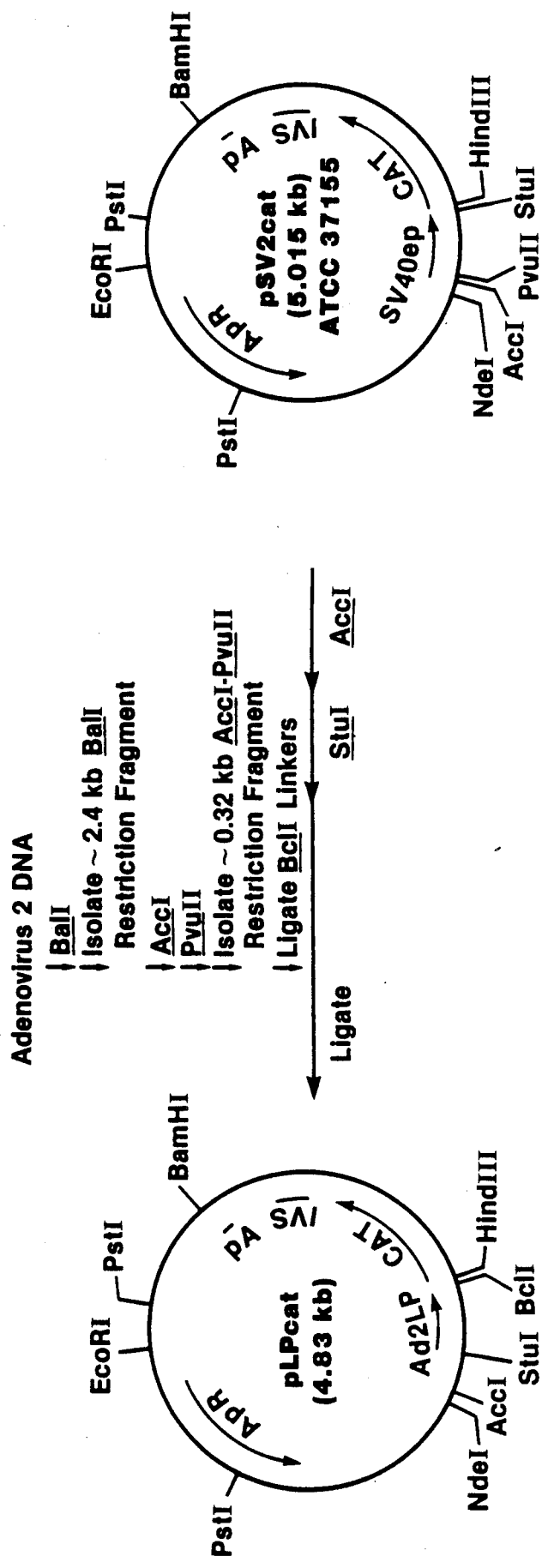

The Construction of Plasmid pBLcat

The Construction of Plasmid pLPC

Construction of Plasmid pL133

VECTORS AND COMPOUNDS FOR DIRECT EXPRESSION OF ACTIVATED HUMAN PROTEIN C

SUMMARY OF THE INVENTION

The present invention provides novel DNA compounds and recombinant DNA cloning vectors that encode human protein C activity. These vectors provide a simple and efficient means for expressing human protein C in its active form. Prior art methods for producing protein C involved the production of an inactive form of protein C (a zymogen), which requires treatment with high levels of thrombin, or thrombin and thrombomodulin, or other expensive enzymes for activation. The present invention provides a method for producing activated protein C that avoids this cumbersome activation step by providing vectors that, due to the introduction of proteolytic cleavage-site-encoding DNA into the protein C coding sequence, lead to the direct expression of activated protein C in recombinant host cells.

BACKGROUND OF THE INVENTION

The Role of Protein C in the Regulation of Blood Coagulation

Protein C, a vitamin K dependent plasma protein, is of major physiological importance in the control of hemostasis. Protein C is synthesized as an inactive molecule, herein called nascent protein C. Nascent protein C undergoes complex processing, giving rise to a number of different inactive molecules as is more fully described below. Inactive, secreted forms of protein C are referred to herein as zymogen protein C. Activation of protein C occurs in the blood by a reaction involving a thrombomodulin-thrombin complex. Activated protein C, together with its cofactor protein S, is an anticoagulant of important physiological significance. Activated protein C can prevent intravascular thrombosis and control the extension of existing clots. The mechanism of action of the activated form of protein C and the mechanism of activation of the inactive zymogen into the active protease have been clarified in recent years (for review, see J. E. Gardiner and J. H. Griffin, *Progress in Hematology*, Vol. XIII, pp. 265–278, ed. Elmer B. Brown, Grune and Stratton, Inc., 1983).

The activation of protein C involves thrombin, the final serine protease in the coagulation cascade, and an endothelial cell membrane-associated glycoprotein called thrombomodulin. Thrombomodulin forms a tight, stoichiometric complex with thrombin. Thrombomodulin, when complexed with thrombin, totally changes the functional properties of thrombin. Thrombin normally clots fibrinogen, activates platelets, and converts clotting cofactors V and VIII to their activated forms, Va and VIIIa. Finally, thrombin activates protein C, but only very slowly and inefficiently. In contrast, thrombin complexed with thrombomodulin does not clot fibrinogen, activate platelets, or convert clotting factors V and VIII to their activated counterparts Va and VIIIa, but does become a very efficient activator of protein C. The rate constant of protein C activation by thrombomodulin-thrombin is over 1,000 fold higher than the rate constant for thrombin alone.

To understand how activated protein C down-regulates blood coagulation, the following brief description of the coagulation enzyme system is provided. The coagulation system is best looked at as a chain reaction involving the sequential activation of zymogens into active serine proteases. This chain reaction eventually produces the enzyme thrombin, which through limited proteolysis converts plasma fibrinogen into the insoluble gel fibrin. Two key events in the coagulation cascade are the conversion of clotting factor X to Xa by clotting factor IXa and the conversion of prothrombin into thrombin by clotting factor Xa. Both of these reactions occur on cell surfaces, most notably the platelet surface, and both reactions require cofactors. The major cofactors, factors V and VIII, in the system circulate as relatively inactive precursors, but when the first few molecules of thrombin are formed, thrombin loops back and activates the cofactors through limited proteolysis. The activated cofactors, Va and VIIIa, accelerate both the conversion of prothrombin into thrombin and also the conversion of factor X to factor Xa by approximately five orders of magnitude. Activated protein C preferentially acts on, to proteolytically degrade, hydrolyze, and irreversibly destroy clotting cofactors Va and VIIIa, the activated forms of the inactive clotting factors V and VIII. Clotting factors V and VIII, in contrast, are very poor substrates for activated protein C.

An important cofactor for activated protein C is protein S, another vitamin K-dependent plasma protein. Protein S substantially increases activated protein C-mediated hydrolysis of factors Va and VIIIa 25 fold.

Protein C as a Therapeutic Agent

Protein C is recognized as a valuable therapeutic agent (see, for example, European Patent Publications Nos. 0215548 and 0191606, incorporated herein by reference). Activated protein C is a novel antithrombotic agent with a wider therapeutic index than available anticoagulants, such as heparin and the oral hydroxycoumarin type anticoagulants. Neither zymogen protein C nor activated protein C is effective until thrombin is generated, because thrombin is needed to convert clotting factors V to Va and VIII to VIIIa; the activated forms of these two cofactors are the preferred substrate for activated protein C. Thrombin is also required to activate zymogen protein C, for without the thrombomodulin-thrombin complex, the protein C zymogen is not converted into its active counterpart.

Activated protein C is an on-demand anticoagulant, because activated protein C works by inactivating cofactors Va and VIIIa. Because thrombin is required to convert factors V and VIII to their activated counterparts Va and VIIIa, protein C only acts as an anticoagulant after thrombin is generated. Conventional anticoagulants, in contrast to activated protein C, maintain a constant anticoagulant state throughout the circulation for as long as they are given to the patient, thereby substantially increasing the risk of bleeding complications over that for protein C or activated protein C. Activated protein C is therefore an on-demand anticoagulant of wide clinical utility for use as an alternative to heparin and the hydroxycoumarins.

In some disease states, such as hereditary protein C deficiency, protein C zymogen is of great therapeutic importance. In congenital homozygous protein C deficiency, affected individuals die in early childhood from purpura fulminans, an often lethal form of disseminated intravascular coagulation. In heterozygous protein C deficiency, affected individuals suffer severe, recurrent thromboembolic episodes. It is well established clinically that plasma protein concentrates designed to treat hemophilia B or factor IX deficiency, which contain protein C as an impurity, are effective in the prevention and treatment of intravascular clotting in heterozygous protein C deficiency. Protein C levels have also been noted to be abnormally low in thrombotic states such as disseminated intravascular coagulation and in disease states predisposing to thrombosis, such as major trauma, major surgery, and cancer.

Although the zymogen forms of protein C are quite useful for therapeutic purposes, some disease states can be treated much more effectively by delivering the activated form of protein C to the patient. For instance, in disease states such as myocardial infarction or deep vein thrombosis (especially as occurs after surgery on the lower extremities), patients have normal levels of protein C zymogen yet not enough activated protein C to prevent the generation of thrombi or to support the removal of existing thrombi. The inability to generate sufficient amounts of activated protein C may arise from inadequate thrombomodulin levels, but, whatever the cause, effective treatment of these disease states requires the administration of activated protein C and not the zymogen. The present invention provides novel compounds and methods for using recombinant DNA technology to produce activated human protein C.

The Synthesis and Activation of Human Protein C

To facilitate an understanding of the activation of protein C and of the invention, the coding sequence, and corresponding amino acid residue sequence, for nascent human protein C is depicted below.

```
         10              20              30              40
ATG TGG CAG CTC ACA AGC CTC CTG CTG TTC GTG GCC ACC TGG GGA ATT
MET TRP GLN LEU THR SER LEU LEU LEU PHE VAL ALA THR TRP GLY ILE
                 5              10             15

50              60              70              80              90
TCC GGC ACA CCA GCT CCT CTT GAC TCA GTG TTC TCC AGC AGC GAG CGT
SER GLY THR PRO ALA PRO LEU ASP SER VAL PHE SER SER SER GLU ARG
            20              25              30

100             110             120             130             140
GCC CAC CAG GTG CTG CGG ATC CGC AAA CGT GCC AAC TCC TTC CTG GAG
ALA HIS GLN VAL LEU ARG ILE ARG LYS ARG ALA ASN SER PHE LEU GLU
         35              40              45

150             160             170             180             190
GAG CTC CGT CAC AGC AGC CTG GAG CGG GAG TGC ATA GAG GAG ATC TGT
GLU LEU ARG HIS SER SER LEU GLU ARG GLU CYS ILE GLU GLU ILE CYS
         50              55              60

200             210             220             230             240
GAC TTC GAG GAG GCC AAG GAA ATT TTC CAA AAT GTG GAT GAC ACA CTG
ASP PHE GLU GLU ALA LYS GLU ILE PHE GLN ASN VAL ASP ASP THR LEU
 65              70              75                              80

250             260             270             280
GCC TTC TGG TCC AAG CAC GTC GAC GGT GAC CAG TGC TTG GTC TTG CCC
ALA PHE TRP SER LYS HIS VAL ASP GLY ASP GLN CYS LEU VAL LEU PRO
             85              90                         95

290             300             310             320             330
TTG GAG CAC CCG TGC GCC AGC CTG TGC TGC GGG CAC GGC ACG TGC ATC
LEU GLU HIS PRO CYS ALA SER LEU CYS CYS GLY HIS GLY THR CYS ILE
            100             105                    110

340             350             360             370             380
GAC GGC ATC GGC AGC TTC AGC TGC GAC TGC CGC AGC GGC TGG GAG GGC
ASP GLY ILE GLY SER PHE SER CYS ASP CYS ARG SER GLY TRP GLU GLY
         115                     120                 125

390             400             410             420             430
CGC TTC TGC CAG CGC GAG GTG AGC TTC CTC AAT TGC TCG CTG GAC AAC
ARG PHE CYS GLN ARG GLU VAL SER PHE LEU ASN CYS SER LEU ASP ASN
         130                 135                 140

440             450             460             470             480
GGC GGC TGC ACG CAT TAC TGC CTA GAG GAG GTG GGC TGG CGG CGC TGT
GLY GLY CYS THR HIS TYR CYS LEU GLU GLU VAL GLY TRP ARG ARG CYS
145                     150                     155                 160

490             500             510             520
AGC TGT GCG CCT GGC TAC AAG CTG GGG GAC GAC CTC CTG CAG TGT CAC
SER CYS ALA PRO GLY TYR LYS LEU GLY ASP ASP LEU LEU GLN CYS HIS
                 165                     170                 175

530             540             550             560             570
CCC GCA GTG AAG TTC CCT TGT GGG AGG CCC TGG AAG CGG ATG GAG AAG
PRO ALA VAL LYS PHE PRO CYS GLY ARG PRO TRP LYS ARG MET GLU LYS
            180                     185                 190
```

-continued

```
      580         590         600         610         620
AAG CGC AGT CAC CTG AAA CGA GAC ACA GAA GAC CAA GAA GAC CAA GTA
LYS ARG SER HIS LEU LYS ARG ASP THR GLU ASP GLN GLU ASP GLN VAL
        195                 200                 205

630         640         650         660         670
GAT CCG CGG CTC ATT GAT GGG AAG ATG ACC AGG CGG GGA GAC AGC CCC
ASP PRO ARG LEU ILE ASP GLY LYS MET THR ARG ARG GLY ASP SER PRO
        210                 215                 220

680         690         700         710         720
TGG CAG GTG GTC CTG CTG GAC TCA AAG AAG AAG CTG GCC TGC GGG GCA
TRP GLN VAL VAL LEU LEU ASP SER LYS LYS LYS LEU ALA CYS GLY ALA
225                 230                 235                 240

730         740         750         760
GTG CTC ATC CAC CCC TCC TGG GTG CTG ACA GCG GCC CAC TGC ATG GAT
VAL LEU ILE HIS PRO SER TRP VAL LEU THR ALA ALA HIS CYS MET ASP
        245                 250                 255

770         780         790         800         810
GAG TCC AAG AAG CTC CTT GTC AGG CTT GGA GAG TAT GAC CTG CGG CGC
GLU SER LYS LYS LEU LEU VAL ARG LEU GLY GLU TYR ASP LEU ARG ARG
        260                 265                 270

820         830         840         850         860
TGG GAG AAG TGG GAG CTG GAC CTG GAC ATC AAG GAG GTC TTC GTC CAC
TRP GLU LYS TRP GLU LEU ASP LEU ASP ILE LYS GLU VAL PHE VAL HIS
        275                 280                 285

870         880         890         900         910
CCC AAC TAC AGC AAG AGC ACC ACC GAC AAT GAC ATC GCA CTG CTG CAC
PRO ASN TYR SER LYS SER THR THR ASP ASN ASP ILE ALA LEU LEU HIS
        290                 295                 300

920         930         940         950         960
CTG GCC CAG CCC GCC ACC CTC TCG CAG ACC ATA GTG CCC ATC TGC CTC
LEU ALA GLN PRO ALA THR LEU SER GLN THR ILE VAL PRO ILE CYS LEU
305                 310                 315                 320

970         980         990         1000
CCG GAC AGC GGC CTT GCA GAG CGC GAG CTC AAT CAG GCC GGC CAG GAG
PRO ASP SER GLY LEU ALA GLU ARG GLU LEU ASN GLN ALA GLY GLN GLU
        325                 330                 335

1010        1020        1030        1040        1050
ACC CTC GTG ACG GGC TGG GGC TAC CAC AGC AGC CGA GAG AAG GAG GCC
THR LEU VAL THR GLY TRP GLY TYR HIS SER SER ARG GLU LYS GLU ALA
        340                 345                 350

1060        1070        1080        1090        1100
AAG AGA AAC CGC ACC TTC GTC CTC AAC TTC ATC AAG ATT CCC GTG GTC
LYS ARG ASN ARG THR PHE VAL LEU ASN PHE ILE LYS ILE PRO VAL VAL
        355                 360                 365

1110        1120        1130        1140        1150
CCG CAC AAT GAG TGC AGC GAG GTC ATG AGC AAC ATG GTG TCT GAG AAC
PRO HIS ASN GLU CYS SER GLU VAL MET SER ASN MET VAL SER GLU ASN
370                 375                 380

1160        1170        1180        1190        1200
ATG CTG TGT GCG GGC ATC CTC GGG GAC CGG CAG GAT GCC TGC GAG GGC
MET LEU CYS ALA GLY ILE LEU GLY ASP ARG GLN ASP ALA CYS GLU GLY
385                 390                 395                 400

1210        1220        1230        1240
GAC AGT GGG GGG CCC ATG GTC GCC TCC TTC CAC GGC ACC TGG TTC CTG
ASP SER GLY GLY PRO MET VAL ALA SER PHE HIS GLY THR TRP PHE LEU
                405                 410                 415

1250        1260        1270        1280        1290
GTG GGC CTG GTG AGC TGG GGT GAG GGC TGT GGG CTC CTT CAC AAC TAC
VAL GLY LEU VAL SER TRP GLY GLU GLY CYS GLY LEU LEU HIS ASN TYR
        420                 425                 430

1300        1310        1320        1330        1340
GGC GTT TAC ACC AAA GTC AGC CGC TAC CTC GAC TGG ATC CAT GGG CAC
GLY VAL TYR THR LYS VAL SER ARG TYR LEU ASP TRP ILE HIS GLY HIS
        435                 440                 445
```

```
                1350         1360          1370         1380
         ATC AGA GAC AAG GAA GCC CCC CAG AAG AGC TGG GCA CCT TAG
         ILE ARG ASP LYS GLU ALA PRO GLN LYS SER TRP ALA PRO ???
          450                 455              460
``` wherein A is deoxyadenyl, G is deoxyguanyl, C is deoxycytidyl, T is thymidyl, ALA is Alanine, ARG is Arginine, ASN is Asparagine, ASP is Aspartic acid, CYS is Cysteine, GLN is Glutamine, GLU is Glutamic Acid, GLY is Glycine, HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

The DNA sequence depicted above was derived from cDNA clones prepared from human liver mRNA that encodes human protein C. Those skilled in the art recognize that the degenerate nature of the genetic code enables one to construct many different DNA sequences that encode the same amino acid residue sequence. The cDNA sequence for nascent human protein C depicted above is thus only one of many possible nascent human protein C-encoding sequences. In constructing the cDNA clones, a 5' poly G sequence, a 3' poly C sequence, and both 5' and 3' PstI restriction enzyme recognition sequences were constructed at the ends of the protein C-encoding cDNA. Two of these cDNA clones were manipulated to construct a DNA molecule comprising both the coding sequence of nascent human protein C and also portions of the DNA encoding the untranslated mRNA at the 5' and 3' ends of the coding region. This DNA molecule was inserted into the PstI site of plasmid pBR322 to construct plasmid pHC7. Plasmid pHC7 thus comprises the coding sequence above and, again depicting only one strand of the molecule, also contains these additional sequences:

```
5'-C   TGC AGG GGG GGG GGG GGG GGG GGG CTG TCA TGG CGG CAG GAC
       GGC GAA CTT GCA GTA TCT CCA CGA CCC GCC CCT ACA GGT GCC
       ACT GCC TCC AGA-3'
and
5'-    CGA CCC TCC CTG CAG GGC TGG GCT TTT GCA TGG CAA TGG ATG GGA
       CAT TAA AGG GAC ATG TAA CAA GCA CAC CCC CCC CCC CCC CCC CCC
       CCC CCC CCT GCA G-3'
``` at the 5' and 3' ends, respectively, of the coding strand of the nascent human protein C coding sequence. Due to the complementary nature of DNA base-pairing, the sequence of one strand of a double-stranded DNA molecule is sufficient to determine the sequence of the opposing strand. Plasmid pHC7 can be conventionally isolated from *E. coli* K12 RR1/pHC7, a strain deposited with and made part of the permanent stock culture collection of the Northern Regional Research Laboratory (NRRL), Peoria, Illinois. A culture of *E. coli* K12 RR1/pHC7 can be obtained from the NRRL under the accession number NRRL B-15926. A restriction site and function map of plasmid pHC7 is presented in FIG. 2 of the accompanying drawings.

Nascent protein C can also be depicted schematically, as shown below.

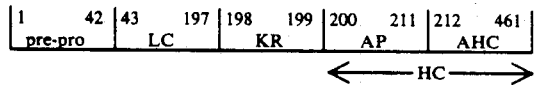

pre-pro—amino acid residues 1–42 of nascent human protein C encode the signal peptide and propeptide of human protein C, important for directing secretion and γ-carboxylation of protein C.

LC—amino acid residues 43–197 of nascent protein C, once post-translationally modified, constitute the light chain (LC) of both the two-chain zymogen (formed from one-chain zymogen by removal of the KR dipeptide, as discussed below) and activated forms of protein C.

KR—amino acid residues 198–199 of nascent human protein C; these residues are believed to be removed (on the basis of homology with bovine protein C), probably by a two-step process comprising a first cleavage (either between residues 197–198 or 199–200) followed by carboxypeptidase or aminopeptidase action, to form two-chain protein C.

AP—amino acid residues 200–211 of nascent protein C constitute the activation peptide, which is removed from the zymogen forms of protein C to obtain activated protein C.

AHC—amino acid residues 212–461 of nascent protein C, once post-translationally modified, constitute the activated heavy chain (AHC) of active protein C.

HC—the heavy chain of the two chain form of protein C zymogen, once post-translationally modified, which constitutes amino acid residues 200–461, the AP and AHC.

Human protein C zymogen is a serine protease precursor synthesized in the liver and present in the blood. For expression of complete biological activity, protein C requires post-translational modifications for which vitamin K is needed. The mature, two-chain, disulfide-linked, protein C zymogen arises from a single-chain precursor by limited proteolysis. This limited proteolysis is believed to include cleavage and removal of a pre-pro peptide consisting of amino acid residues 1–42 during intracellular processing and secretion of the nascent polypeptide from the cell and removal of amino acid residues 198 and 199 to form the two chains observed in the zymogen. The activation of the zymogen into the active serine protease involves the proteolytic cleavage of an ARG-LEU peptide bond (residues 211 and 212). This latter cleavage releases a dodecapeptide (residues 200–211) that constitutes the amino-terminus of the larger (heavy) chain of the two-chain zymogen molecule. Protein C is significantly glycosylated; the mature enzyme contains ~23% carbohydrate. Protein C also contains a number of unusual amino acids, including γ-carboxyglutamic acid and β-hydroxyaspartic acid (erythro-L-β-hydroxy aspartate). γ-carboxyglutamic acid (gla) is produced by γ-glutamyl carboxylation from glutamic acid residues with the aid of a hepatic microsomal carboxylase which requires vitamin K as a cofactor.

The activation of human protein C can also be represented schematically and is shown below. Those skilled in the art recognize that the order of the steps shown in the schematic do not necessarily reflect the in vivo pathway.

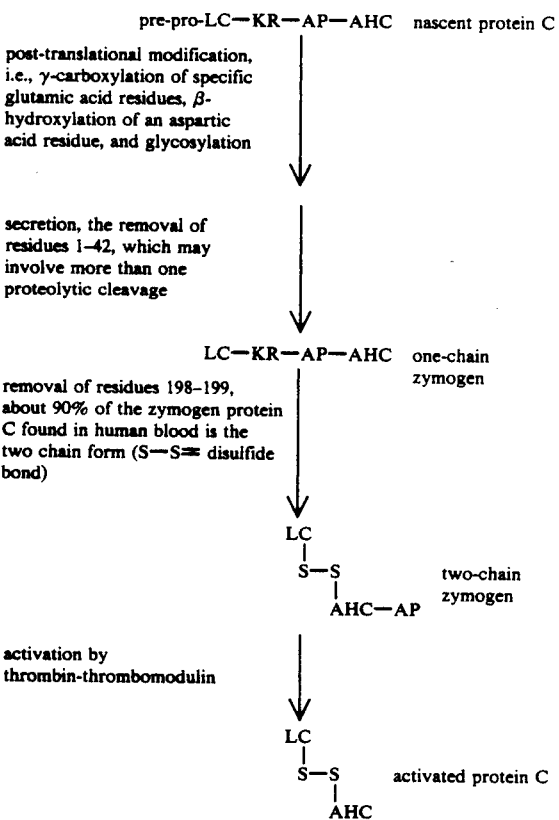

The present invention provides novel compounds, vectors, transformants, and methods for the direct expression of recombinant activated protein C.

Definitions

For purposes of the present invention, as disclosed and claimed herein, the following terms are as defined below.

Ad2LP—the major late promoter of adenovirus type 2.

Amino acid residues in proteins or peptides described herein as abbreviated as follows:

| Three-Letter Abbreviation | Amino Acid Residue | One-Letter Abbreviation |
|---|---|---|
| PHE | Phenylalanine | F |
| LEU | Leucine | L |
| ILE | Isoleucine | I |
| MET | Methionine | M |
| VAL | Valine | V |
| SER | Serine | S |
| PRO | Proline | P |
| THR | Threonine | T |
| ALA | Alanine | A |
| TYR | Tyrosine | Y |
| HIS | Histidine | H |
| GLN | Glutamine | Q |
| ASN | Asparagine | N |
| LYS | Lysine | K |
| ASP | Aspartic Acid | D |
| GLU | Glutamic Acid | E |
| CYS | Cysteine | C |
| TRP | Tryptophan | W |
| ARG | Arginine | R |
| GLY | Glycine | G |

ApR—the ampicillin-resistant phenotype or gene conferring same.

BK—DNA from BK virus.

CAT—the chloramphenicol acetyltransferase gene.

Enh or enhancer—the enhancer of BK virus.

ep or SV40ep—a DNA segment comprising the SV40 early promoter of the T-antigen gene, the T-antigen binding sites, the SV40 enhancer, and the SV40 origin of replication.

γ-carboxylation—a reaction which adds a carboxyl group to glutamic acids at the γ-carbon.

γ-carboxylated protein—a protein in which some glutamic acids residues have undergone γ-carboxylation.

IVS—DNA encoding an intron, also called an intervening sequence.

MMTpro—the promoter of the mouse metallothionein-I gene.

Nascent protein—the polypeptide produced upon translation of a mRNA transcript, prior to any post-translational modifications. However, post-translational modifications such as γ-carboxylation of glutamic acid residues and hydroxylation of aspartic acid residues may occur before a protein is fully translated from an mRNA transcript.

NeoR—a neomycin resistance-conferring gene, which can also be used to confer resistance to the antibiotic G418.

pA—a DNA sequence encoding a polyadenylation signal.

Promoter—a DNA sequence that directs transcription of DNA into RNA.

Protein C activity—any property of human protein C responsible for proteolytic, amidolytic, esterolytic, and biological (anticoagulant or profibrinolytic) activities. Methods for testing for protein anticoagulant activity are well known in the art, i.e., see Grinnell et al., 1987, Biotechnology 5:1189.

Recombinant DNA Cloning Vector—any agent, including, but not limited to; chromosomally integrating agents, autonomously replicating plasmids, and phages, comprising a DNA molecule to which one or more additional DNA segments can be or have been added.

Recombinant DNA Expression Vector—any recombinant DNA cloning vector into which a promoter has been incorporated.

Recombinant DNA Vector—any recombinant DNA cloning or expression vector.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

Structural Gene—any DNA sequence that encodes a functional polypeptide, inclusive of translational start and stop signals.

TcR—the tetracycline-resistant phenotype or gene conferring same.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding and translational start codon, such as 5'-ATG-3', that provides for the translation of a mRNA transcript into a peptide or polypeptide.

Zymogen—an enzymatically inactive precursor of a proteolytic enzyme. Protein C zymogen, as used herein, refers to secreted, inactive forms, whether one chain or two chain, of protein C.

BRIEF DESCRIPTION OF THE FIGURES

FIG. 1, Part A depicts the construction of plasmid pBKneoI from BK virus and plasmid pdBPV-MMtneo.

FIG. 1, Part B depicts the construction of plasmid pLPcat from adenovirus 2 and plasmid pSV2cat.

FIG. 1, Part C depicts the construction of plasmid pBLcat from plasmid pBKneoI and plasmid pLPcat.

FIG. 1, Part D depicts the construction of plasmid pLPC from plasmid pBLcat and plasmid pL133.

DETAILED DESCRIPTION OF THE INVENTION

Figure 1A:
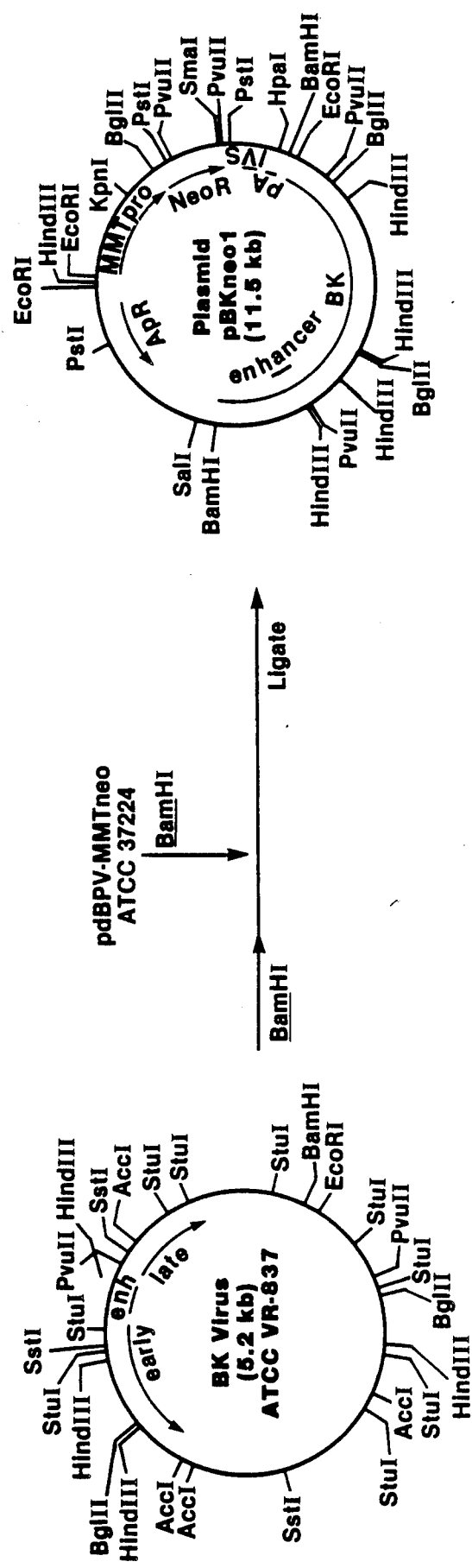
FIG. 1 consists of four parts and schematically illustrates the construction protocol for plasmid pLPC, a starting material used in the construction of plasmid pLAPC of the invention.

The present invention provides novel DNA compounds that code for the expression of activated human protein C. Although several methods of producing human protein C zymogen and nascent human protein C have been described (see European Patent Publications 215548 and 191606), these methods do not provide for the direct expression of activated human protein C. Instead, the protein C zymogen produced by these methods must be treated with substances such as α-thrombin, trypsin, Russell's viper venom factor X activator, or a mixture of thrombin and thrombomodulin to obtain activated protein C. All of these activation methods introduce inefficiency, risk of contamination, and higher costs to the recombinant production of activated human protein C. In addition, some of the activation reactions must be closely monitored so that the proteolysis stops after the proteolytic cleavage of the activation peptide—otherwise, the activated protein C produced is cleaved and rendered inactive. The present invention provides DNA compounds, recombinant DNA expression vectors, transformed cell lines, and methods for the direct expression of recombinant activated human protein C.

The present invention provides a method for producing recombinant activated protein C directly upon secretion from a eukaryotic host cell, which comprises:

(A) transforming said host cell with a recombinant DNA vector, said vector comprising:
  (i) a DNA sequence that encodes an amino acid residue sequence, said amino residue sequence comprising, from the amino-terminus to the carboxy terminus:
    (a) a signal peptide and pro-peptide of a γ-carboxylated, secreted protein;
    (b) the light chain of human protein C;
    (c) a dipeptide selected from lysinearginine, lysine-lysine, or arginine-arginine;
    (d) a cleavage sequence for a cell associated protease; and
    (e) the activated heavy chain of human protein C; and
  (ii) a promoter positioned to drive expression of said DNA sequence; and (B) culturing said host cell transformed in step (A) under conditions that allow for expression of said DNA sequence, subject to the limitation that said cleavage sequence is not the activation peptide of human protein C zymogen.

The invention provides novel DNA compounds for use in the method of producing activated protein C. These novel compounds all encode a pre-propeptide comprising a signal peptide for directing secretion and a propeptide from a γ-carboxylated (through the action of a vitamin K-dependent carboxylase) protein. Such propeptide sequences are well-known in the art. See, for example, Suttie et al., 1987, Proc. Natl. Acad. Sci. 84:634–637. Preferably, and for ease of construction, both the signal peptide coding sequence and the propeptide coding sequence will be derived from the amino acid residue sequence of the pre-propeptide of a γ-carboxylated protein. Examples of such γ-carboxylated proteins include, but are not limited to, factor VII, factor IX, factor X, prothrombin, protein S, protein Z, and, most preferably, protein C.

The DNA compounds of the invention further comprise the coding sequence for the light chain of human protein C positioned immediately adjacent to, downstream of, and in translational reading frame with the pre-propeptide coding sequence. The light chain of human protein C contains amino acid residues 43 to 197, inclusive, of nascent protein C, as depicted in the background section above. The amino-terminal portions of the vitamin K-dependent plasma proteins, such as the amino-terminal portion of the light chain of protein C, are responsible for calcium-binding activity of these proteins. The calcium-binding domains of these plasma proteins, such as factor VII, factor IX, factor X, prothrombin, and protein S, are interchangeable (see European Patent Publication No. 0215548A1, at pages 12 and 13) and equivalent to the calcium-binding domain of the light chain of human protein C.

The DNA compounds of the invention further comprise the coding sequence for the dipeptide LYS-ARG (KR) positioned immediately adjacent to, downstream of, and in translational reading frame with the light chain coding sequence. A dibasic dipeptide such as LYS-ARG is positioned in the nascent protein between the carboxyl-terminal side of the light chain and the amino-terminal side of the cleavage sequence for a cell-associated protease. The orientation of the LYS-ARG dipeptide in the expressed protein is irrelevant for purposes of the present invention. Dibasic dipeptides such as LYS-LYS or ARG-ARG are equivalent to the LYS-ARG dipeptide for purposes of the present invention.

Immediately downstream of the codons for the LYS-ARG dipeptide is the coding sequence for a proteolytic cleavage sequence. In nature, positioned at the carboxy-terminal end of the LYS-ARG dipeptide of human protein C, there is a 12 amino acid residue peptide, the activation peptide, that is removed by proteolytic cleavage. However, a key feature of the DNA compounds of the present invention is that the presence of the activation peptide coding sequence is not required. The preferred DNA compounds of the present invention do not contain the coding sequence for the activation peptide. Instead, in these preferred compounds, the AP coding sequence is replaced with a coding sequence for a proteolytic cleavage sequence for a cell associated protease.

Because the object of the present invention is to produce activated protein C directly from recombinant cells, cleavage of the light chain of protein C from the activated heavy chain of protein C must take place either in the cell or on the surface of the cell upon secretion. For purposes of the present invention, a cell associated protease includes not only proteases located in the cytoplasm or organelles of a cell, but also proteases located in the cell membranes that can cleave proteins during or immediately upon secretion. Consequently, the present invention provides DNA compounds that encode a proteolytic cleavage sequence for a cell associated protease for purposes of separating the light and activated heavy chains of human protein C.

A variety of proteolytic cleavage sequences for cell associated proteases are known in the art. Cleavage sequences are amino acid sequences adjacent to cleavage sites for cell associated proteases. Table I, below, provides an illustrative but non-exhaustive listing of such cleavage sequences suitable for use as the cleavage sequence for a cell associated protease in the methods and compounds of the present invention.

TABLE I

| Proteolytic Cleavage Sequences for Cell Associated Proteases | |
|---|---|
| Origin | Sequence (using single-letter abbreviation) |
| Cleavage sequences recognized by cell associated proteases so as to generate a two-chain molecule from a one-chain molecule include: | |
| insulin receptor | PRPSRKRR |
| protein C | KKRSHLKR |
| factor X | QTLERRKR |
| insulin | LEGSLQKR and FYTPKTRR |
| Cleavage sequences recognized by cell associated proteases so as to generate the removal of the propeptide from secreted proteins include: | |
| glucagon | MLVQGSWQ |
| protein C | QVLRIRKR |
| factor IX | KILNRPKR |
| factor X | NILARVTR |
| tissue plasminogen activator | ARFRRGAR |
| Cleavage sequences recognized by cell associated proteases so as to generate oligopeptides from a polypeptide, i.e., preproglucagon, include: | |
| amino-terminal peptide | DQMNEDKR |
| glucagon | QWLMNTKR |
| spacer peptide 1 | NRDDIAKR |
| GLP1 | LVKGRGRR |
| spacer peptide 2 | IVEELGRR |

Additional cleavage sequences for cell associated proteases suitable for use in the invention are exemplified in Schwartz, 1986, FEBS 200(1):1. In addition, any peptide-encoding sequence, naturally occurring or synthetic, containing a dibasic dipeptide at the C-terminus would constitute a cleavage sequence for a cell associated protease. Of the cleavage sequences listed in Table 1, the cleavage sequence that is cleaved to form the two-chain insulin receptor molecule is most preferred for purposes of the present invention.

Those skilled in the art will recognize that the number of amino acid residues in the cleavage sequence can be varied somewhat. In the method of the present invention to produce activated protein C, the nascent protein is cleaved at the carboxy-terminus of the light chain (at the KR dipeptide) and also cleaved at the amino-terminus of the activated heavy chain. Therefore, the residues in between the KR dipeptide and the proteolytic cleavage site (located at the amino-terminus of the activated heavy chain) will be removed during processing of the polypeptide. Because these two proteolytic cleavage reactions will remove everything between the carboxy-terminus of the light chain and the amino-terminus of the heavy chain, the proteolytic cleavage sequence can contain additional residues without affecting the nature of the end product, activated protein C. Therefore, cleavage sequences longer than those shown in Table I can be used in the method and compounds of the invention. In addition, although the cleavage sequences shown above all contain eight residues, all eight residues may not be required, and shorter sequences can be used in the method and compounds of the invention.

Immediately adjacent to, downstream of, and in translational reading frame with the coding sequence for the proteolytic cleavage sequence in the DNA sequences of the invention is the coding sequence for the activated heavy chain of human protein C. As stated in the background section of the invention, the activated heavy chain of human protein C consists of residues 212 through 461 of nascent human protein C.

Depicted below is the amino acid residue sequence of the unprocessed, nascent polypeptide translated from the mRNA transcript generated from the preferred DNA coding sequence of the invention. The polypeptide begins with the pre-propeptide of human protein C, followed by the light chain of human protein C, followed by the LYS-ARG dipeptide, followed by the insulin receptor cleavage sequence (IRS), followed by activated heavy chain of human protein C. Shown schematically, the polypeptide is:

| pre-pro | LC | KR | IRS | AHC |

The amino acid residue sequence of the polypeptide is:

H2N— MET TRP GLN LEU THR SER LEU LEU LEU PHE VAL ALA THR TRP GLY ILE
SER GLY THR PRO ALA PRO LEU ASP SER VAL PHE SER SER SER GLU ARG
ALA HIS GLN VAL LEU ARG ILE ARG LYS ARG ALA ASN SER PHE LEU GLU

-continued

```
GLU LEU ARG HIS SER SER LEU GLU ARG GLU CYS ILE GLU GLU ILE CYS
ASP PHE GLU GLU ALA LYS GLU ILE PHE GLN ASN VAL ASP ASP THR LEU
ALA PHE TRP SER LYS HIS VAL ASP GLY ASP GLN CYS LEU VAL LEU PRO
LEU GLU HIS PRO CYS ALA SER LEU CYS CYS GLY HIS GLY THR CYS ILE
ASP GLY ILE GLY SER PHE SER CYS ASP CYS ARG SER GLY TRP GLU GLY
ARG PHE CYS GLN ARG GLU VAL SER PHE LEU ASN CYS SER LEU ASP ASN
GLY GLY CYS THR HIS TYR CYS LEU GLU GLU VAL GLY TRP ARG ARG CYS
SER CYS ALA PRO GLY TYR LYS LEU GLY ASP ASP LEU LEU GLN CYS HIS
PRO ALA VAL LYS PHE PRO CYS GLY ARG PRO TRP LYS ARG MET GLU LYS
LYS ARG SER HIS LEU LYS ARG PRO ARG PRO SER ARG LYS ARG ARG LEU
ILE ASP GLY LYS MET THR ARG ARG GLY ASP SER PRO TRP GLN VAL VAL
LEU LEU ASP SER LYS LYS LYS LEU ALA CYS GLY ALA VAL LEU ILE HIS
PRO SER TRP VAL LEU THR ALA ALA HIS CYS MET ASP GLU SER LYS LYS
LEU LEU VAL ARG LEU GLY GLU TYR ASP LEU ARG ARG TRP GLU LYS TRP
GLU LEU ASP LEU ASP ILE LYS GLU VAL PHE VAL HIS PRO ASN TYR SER
LYS SER THR THR ASP ASN ASP ILE ALA LEU LEU HIS LEU ALA GLN PRO
ALA THR LEU SER GLN THR ILE VAL PRO ILE CYS LEU PRO ASP SER GLY
LEU ALA GLU ARG GLU LEU ASN GLN ALA GLY GLN GLU THR LEU VAL THR
GLY TRP GLY TYR HIS SER SER ARG GLU LYS GLU ALA LYS ARG ASN ARG
THR PHE VAL LEU ASN PHE ILE LYS ILE PRO VAL VAL PRO HIS ASN GLU
CYS SER GLU VAL MET SER ASN MET VAL SER GLU ASN MET LEU CYS ALA
GLY ILE LEU GLY ASP ARG GLN ASP ALA CYS GLU GLY ASP SER GLY GLY
PRO MET VAL ALA SER PHE HIS GLY THR TRP PHE LEU VAL GLY LEU VAL
SER TRP GLY GLU GLY CYS GLY LEU LEU HIS ASN TYR GLY VAL TYR THR
LYS VAL SER ARG TYR LEU ASP TRP ILE HIS GLY HIS ILE ARG ASP LYS
GLU ALA PRO GLN LYS SER TRP ALA PRO—COOH
```

Those skilled in the art will recognize that, due to the degeneracy of the genetic code, a variety of DNA compounds can encode the polypeptide depicted above. Consequently, the constructions described below and in the accompanying Examples for the preferred DNA compounds, vectors, and transformants of the invention are merely illustrative and do not limit the scope of the invention.

Initial attempts to directly express activated human protein C involved the use of a coding sequence for nascent human protein C from which the AP region had been deleted by site-specific mutagenesis. Shown schematically, this coding sequence had the structure:

| pre-pro | LC | KR | AHC |

As described in the accompanying examples, this coding sequence was inserted into a recombinant DNA expression vector and the resulting vector, designated pLAPC, was transformed into a eukaryotic host cell. The resulting transformant produced normal amounts of two-chain protein C, as measured by reactivity with anti-protein C antibody; however, this material had very low protein C activity. The rationale for the construction of plasmid pLAPC was that whatever proteolytic activity was responsible for cleaving the KR region to form the two-chain zymogen would probably also act to cleave a protein C molecule that lacked the AP region. Two-chain material was observed to result from cells expressing the AP-minus protein C coding sequence, but this material only had low levels of activated human protein C amidolytic activity. In addition to its usefulness in driving expression of activated protein C activity, however, plasmid pLAPC also serves as useful starting material for the construction of other vectors of the invention that drive high-level direct recombinant expression of activated human protein C. The construction protocol for plasmid pLAPC from starting plasmid pHC7 is described in Example 1. Plasmid pHC7 is available from the Northern Regional Research Center (NRRL), Peoria, IL 61604 in *E. coli* K12 RR1/pHC7 under the accession number NRRL B-15926.

Another attempt at directly expressing activated protein C involved the creation of a coding sequence in which a proteolytic cleavage sequence was inserted into the protein C coding sequence between the AP coding sequence and the AHC coding sequence. The proteolytic cleavage site was introduced with a proteolytic cleavage sequence derived from the insulin receptor. Thus, the coding sequence, shown schematically, had the structure:

| pre-pro | LC | KR | AP | IRS | AHC |

This coding sequence was inserted into a vector analogous to plasmid pLAPC to yield plasmid pLPC-IRS. Attempts to introduce plasmid pLPC-IRS into eukaryotic host cells, however, never generated a transformant that produced detectable protein C activity or antigen.

Thus, the present method for directly expressing activated protein C was achieved only after replacing the AP coding sequence with the IRS coding sequence. The resulting coding sequence, shown schematically, had the structure:

| pre-pro | LC | KR | IRS | AHC |

The construction of this coding sequence, in which the AP coding sequence is replaced by the IRS sequence, is described in Example 3. Essentially, the construction involved site-specific mutagenesis of the protein C coding sequence. A portion of the protein C coding sequence comprising the activation peptide-encoding DNA was isolated from plasmid pHC7, inserted into phage M13mp18, and then altered by site-specific mutagenesis. The mutagenized coding sequence was then cloned into a eukaryotic cloning vector to achieve a plasmid, designated pLAPC-IRS, identical to plasmid pLAPC, except for the insertion of the IRS coding sequence between the KR and AHC coding sequences. Plasmid pLAPC-IRS only differs from plasmid pLPC-IRS by deletion of the AP coding sequence. The construction protocol for plasmid pLAPC-IRS is described in detail in Example 3.

The methods of site-specific mutagenesis described in the accompanying Examples are illustrative and can be used to generate other compounds of the invention in which the IRS coding sequence is replaced with a different coding sequence for a proteolytic cleavage site of a cell associated protease. The DNA compounds of the invention can also be synthesized chemically, or by combining restriction fragments, or by a combination of techniques known in the art. DNA synthesizing machines are also available and can be used to construct the compounds of the invention.

The illustrative vector of the invention, plasmid pLAPC-IRS, comprises the BK enhancer positioned to stimulate transcription by the adenovirus major late promoter of the novel activated protein C coding sequence of the invention. Those skilled in the art recognize that a great number of eukaryotic promoters, enhancers, and expression vectors are known in the art and can be used in the method of the present invention. Those skilled in the art also recognize that a eukaryotic expression vector can function without an enhancer element. The key aspect of the present invention does not reside in the particular enhancer, if any, or promoter, used to drive expression of the activated protein C but rather resides in the use of a proteolytic cleavage sequence in the coding sequence for protein C so as to produce activated protein C directly from recombinant cells.

However, choice of vector elements, such as promoters, enhancers, and selectable markers, can have great impact on the ultimate levels of activated protein C produced by a eukaryotic host cell. U.S. Patent Application Ser. No. 849,999, filed Apr. 9, 1986, incorporated herein by reference, discloses a number of expression vectors for zymogen protein C that utilize the BK enhancer to stimulate a eukaryotic promoter positioned to drive expression of human protein C. These vectors drive especially high expression levels when transformed into eukaryotic cells that also express an immediate-early gene product of a large DNA virus, such as the ElA gene product of adenovirus. As is evident from the illustrative vector pLAPC-IRS disclosed herein, the BK enhancer-E1A gene product expression method of Serial No. 849,999 is especially preferred for use with the vectors of the present invention.

The present invention is not limited to use in a particular eukaryotic host cell. A variety of eukaryotic host cells are available from depositories such as the American Type Culture Collection (ATCC) Rockville, MD 20852, and are suitable for use with the vectors of the invention. The choice of a particular host cell depends to some extent on the particular expression vector used to drive expression of the activated protein C-encoding DNA compounds of the invention. Because protein C zymogen undergoes substantial post-translational modification, however, some host cells are more preferred for use with the vectors of the invention. U.S. Patent Application Ser. No. 849,999 and Grinnell et al., 1987, Bio/Technology 5:1189 disclose that adenovirus-transformed, human embryonic kidney cells are especially preferred for use in the recombinant production of γ-carboxylated proteins such as human protein C. One such adenovirus-transformed, human embryonic kidney cell line is the 293 cell line, available from the ATCC under the accession number CRL 1573. The 293 cell line is also preferred for use with the vectors of the present invention.

However, the advantages of producing a γ-carboxylated protein, such as human protein C, in an adenovirus-transformed cell line are not limited to adenovirus-transformed human embryonic kidney cells. In fact, adenovirus-transformed cells in general are exceptional hosts for the production of γ-carboxylated human protein C. One especially preferred cell line of this type is the AV12-664 (hereinafter "AV12") cell line, available from the ATCC under the accession number ATCC CRL 9595. The AV12 cell line was constructed by injecting a Syrian hamster in the scruff of the neck with human adenovirus 12 and isolating cells from the resulting tumor. Example 4, below, describes the transformation of both the 293 and AV12 cell lines with illustrative vector pTAPC-IRS.

The vectors of the invention can be transformed into and expressed in a variety of eukaryotic, especially mammalian, host cells. Vectors of the invention that possess no selectable marker with which to isolate and identify stable eukaryotic transformants are useful not only for purposes of transient assay but also for purposes of cotransformation, a procedure disclosed in U.S. Pat. No. 4,399,216, issued Aug. 26, 1983, and incorporated herein by reference. The vectors of the invention can also comprise sequences that allow for replication in *E. coli*, as it is usually more efficient to prepare plasmid DNA in *E. coli* than in other host organisms.

Direct expression of the activated human protein C structural gene contained on the vectors of the invention occurs in those host cells in which the particular promoter associated with the structural gene functions. Exemplary host cells suitable for use in the invention are listed in Table II, along with appropriate comments.

TABLE II

| Host Cell | Origin | Source | Comments |
| --- | --- | --- | --- |
| HepG-2 | Human Liver Hepatoblastoma | *ATCC #HB 8065 | U.S. Pat. No. 4,393,133 describes the use of this cell line. |
| CV-1 | African Green Monkey Kidney | ATCC #CCL 70 | |
| LLC-MK$_2$ original | Rhesus Monkey Kidney | ATCC #CCL 7 | |
| LLC-MK$_2$ derivative | Rhesus Monkey Kidney | ATCC #CCL 7.1 | Grows faster than ATCC #CCL 7 |
| 3T3 | Mouse Embryo Fibroblasts | ATCC #CCL 92 | |
| CHO-K1 | Chinese Hamster Ovary | ATCC #CCL 61 | Proline-requiring. Derivatives of CHO-K1, such as the dhfr- derivative DXB11, can be generated from this host. |
| HeLa | Human Cervix Epitheloid | ATCC #CCL 2 | |
| RPMI8226 | Human Myeloma | ATCC #CCL 155 | IgGg lambda-type light chain secreting |
| H4IIEC3 | Rat Hepatoma | ATCC #CRL 1600 | Derivatives, such as 8-azaguanine-resistant FAZA host cells, can be |

TABLE II-continued

| Host Cell | Origin | Source | Comments |
|---|---|---|---|
| | | | generated from this host. |
| C127I | Mouse Fibroblast | ATCC # CRL 1616 | |
| HS-Sultan | Human Plasma Cell Plasmocytoma | ATCC #CRL 1484 | |
| BHK-21 | Baby Hamster Kidney | ATCC #CCL 10 | |

*American Type Culture Collection, 12301 Parklawn Drive, Rockville, Maryland 20852-1776

As indicated by Table II, many mammalian host cells possess the necessary cellular machinery for the recognition and proper processing of the signal peptide and proteolytic cleavage site on the compounds of the invention and provide the post-translational modifications, such as glycosylation, γ-carboxylation, and β-hydroxylation, as are observed in human protein C present in blood plasma. A wide variety of vectors, discussed below, exists for the transformation of such eukaryotic host cells, but the specific vectors exemplified below are in no way intended to limit the scope of the present invention.

The pSV2-type vectors comprise segments of the SV40 genome that constitute a defined eukaryotic transcription unit--promoter (ep), intervening sequence (IVS), and polyadenylation (pA) site. In the absence of SV40 T-antigen, the plasmid pSV2-type vectors transform mammalian and other eukaryotic host cells by integrating into the host cell chromosomal DNA. A variety of plasmid pSV2-type vectors have been constructed (see Eukaryotic Viral Vectors, edited by Gluzman, published by Cold Spring Harbor Laboratories, Cold Spring Harbor, New York, 1982), such as plasmids pSV2-gpt, pSV2-neo, pSV2-dhfr, pSV2-hyg, and pSV2-β-globin, in which the SV40 promoter drives transcription of an inserted gene. These vectors are suitable for use with the coding sequences of the invention and are available either from the American Type Culture Collection (ATCC) in Rockville, Maryland or from the Northern Regional Research Laboratory (NRRL) in Peoria, Illinois.

Plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification, described in a review article by Schimke, 1984, Cell 37:705-713, can involve DNA sequences closely contiguous with the dhfr gene, such as an activated human protein C-encoding sequence of the invention, and thus can be used to increase production of activated protein C.

Plasmids of the present invention which were constructed for expression of activated protein C activity in mammalian and other eukaryotic host cells can utilize a wide variety of promoters. The present invention is in no way limited to the use of the particular eukaryotic promoters exemplified herein. Promoters such as the SV40 late promoter or the eukaryotic promoters disclosed in Bucher et al., 1986, Nuc. Acids Res. 14(24):1009, or promoters from eukaryotic genes, such as, for example, the estrogen-inducible chicken ovalbumin gene, the interferon genes, the glucocorticoid-inducible tyrosine aminotransferase gene, the thymidine kinase gene, and the major early and late adenovirus genes, can be readily isolated and modified for use on recombinant DNA expression vectors designed to produce protein C in eukaryotic host cells. Eukaryotic promoters can also be used in tandem to drive expression of protein C. Furthermore, a large number of retroviruses are known that infect a wide range of eukaryotic host cells. The long terminal repeats in the retrovirus DNA often encode promoter activity and thus can be used to drive expression of activated human protein C.

Plasmid pRSVcat (ATCC 37152) comprises portions of the long terminal repeat of the Rous Sarcoma virus (RSV), a virus known to infect chicken and other host cells. The RSV long terminal repeat sequences can be isolated on an ~0.76 kb NdeI-HindIII restriction fragment of plasmid pRSVcat. The promoter in the RSV long terminal repeat (Gorman et al., 1982, P.N.A.S. 79:6777) is suitable for use in vectors of the invention. Plasmid pMSVi (NRRL B-15929) comprises the long terminal repeats of the Murine Sarcoma virus (MSV), a virus known to infect mouse and other host cells. These repeat sequences are suitable for use as a promoter in the vectors of the invention. The mouse metallothionein (MMT) promoter has also been well characterized for use in eukaryotic host cells and is suitable for use in the vectors of the invention. The MMT promoter is present in the 15 kb plasmid pdBPV-MMTneo (ATCC 37224), which can serve as the starting material for the construction of other plasmids of the present invention.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of human protein C and can be constructed by following conventional synthetic or site specific mutagenesis procedures. Synthetic methods can be carried out in substantial accordance with the procedures of Itakura et al., 1977 Science 198:1056 and Crea et al., 1978, Proc. Nat. Acad. Sci. USA 75:5765. Therefore, the present invention is in no way limited to the DNA sequences and plasmids specifically exemplified.

After transformation of a vector of the invention into a eukaryotic host cell, one can select transformants on the basis of a selectable phenotype. This selectable phenotype can be conferred either by a selectable marker present on the expression vector or present on another vector cotransformed with the expression vector into the host cell. Once transformants are selected, it is desirable to identify which transformants are expressing the highest levels of the desired protein encoded on the expression vector. Such identification is especially important after a cotransformation procedure, which generates a number of transformants that contain only the plasmid containing the selectable marker and so do not contain the expression vector.

The present invention therefore provides a novel method not only for identifying cells that express and secrete a desired protein but also for quantifying, relative to the other cells examined using the method, the amount of protein secreted. The method also allows for the isolation in viable form of the cells secreting the desired protein. Although the method is generally applicable to any secreted protein, it is illustrated herein with particular reference to activated protein C. In addition, although the method is applicable to any cell, whether eukaryotic or prokaryotic or whether transformed or naturally occurring, it is illustrated herein by application to eukaryotic transformants.

This method for identifying and isolating cells that express and secrete a protein and for quantifying, relative to other cells examined by the method, the amount of protein produced comprises (a) obtaining a population of cells on a suitable solid substrate; (b) overlaying said cells with a film of sterile agar; (c) placing a sheet of nitrocellulose on said film; and (d) removing said sheet and detecting said protein bound to said sheet using an antibody against said protein. Any protein-binding membrane, including nylon, DBM, or cellulose acetate can be used in place of the nitrocellulose. In addition, gelatin can be used in place of the agar. This method for identifying cells secreting high levels of protein is more fully described in Example 5 below.

The following Examples illustrate the methods and describe the construction protocols for representative compounds, vectors and transformants of the invention without limiting the same thereto.

EXAMPLE 1

Construction of Plasmid pLAPC

This Example provides a detailed protocol for the construction of plasmid pLAPC. In brief, Example 1A describes the isolation of a DNA fragment encoding a portion of the protein C molecule, including the activation peptide, from plasmid pHC7. Example 1B describes the cloning of this DNA fragment into phage M13mp18 and the removal of the DNA encoding the activation peptide from the resulting recombinant phage by site specific mutagenesis. Example 1C describes the final steps in the construction of plasmid pLAPC, more specifically, the isolation of the mutagenized fragment and its ligation with two fragments derived from plasmid pLPC to yield plasmid pLAPC. The construction protocol for plasmid pLPC is described in Example 2.

A. Isolation of a DNA Fragment Containing the Coding Sequence for the Activation Peptide of Human Protein C Plasmid pHC7 contains the complete coding sequence for nascent human protein C. One liter of L broth (10 g peptone, 10 g NaCl, and 5 g yeast extract) containing 15 μg/ml tetracycline was inoculated with a culture of E. coli K12 RR1/pHC7 (NRRL B-15926) and incubated in an air-shaker incubator at 37° C. until the optical density (O.D.) at 590 nm was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

The culture was centrifuged in a Sorvall GSA rotor (DuPont Co., Instrument Products, Biomedical Division, Newtown, CN 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was again discarded, and the cell pellet was frozen in a dry ice-ethanol bath and then thawed. The thawed cell pellet was resuspended in 10 ml of a 25% sucrose/50 mM EDTA solution. About one ml of a 5 mg/ml lysozyme solution; 3 ml of 0.25 M EDTA, pH=8.0; and 100 μl of 10 mg/ml RNAse A were added to the solution, which was then incubated on ice for 15 minutes. Three ml of lysing solution (prepared by mixing 3 ml 10% Triton-X 100; 75 ml 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, IL 60646). About 30.44 g of CsCl and ~1 ml of a 5 mg/ml ethidium bromide solution were added to the solution, the volume of which was then adjusted to 40 ml. The solution was decanted into a Vti50 ultracentrifuge tube (Beckman). The tube was sealed and then centrifuged in a Vti50 rotor at 42,000 rpm for ~16 hours. The resulting plasmid band, visualized with ultraviolet light, was isolated and then placed in a ti75 tube and rotor (Beckman) and centrifuged at 55,000 rpm for 16 hours. Any necessary volume adjustments were made using TES containing 0.761 g/ml CsCl. The plasmid band was again isolated, the ethidium bromide extracted with salt-saturated isopropanol, and finally diluted 1:3 with TES buffer. Two volumes of ethanol were then added to the solution, and the resulting mixture was incubated overnight at −20° C. The plasmid DNA was pelleted by centrifuging the solution in an SS34 rotor (DuPont Co.) for 15 minutes at 10,000 rpm.

Figure 2:
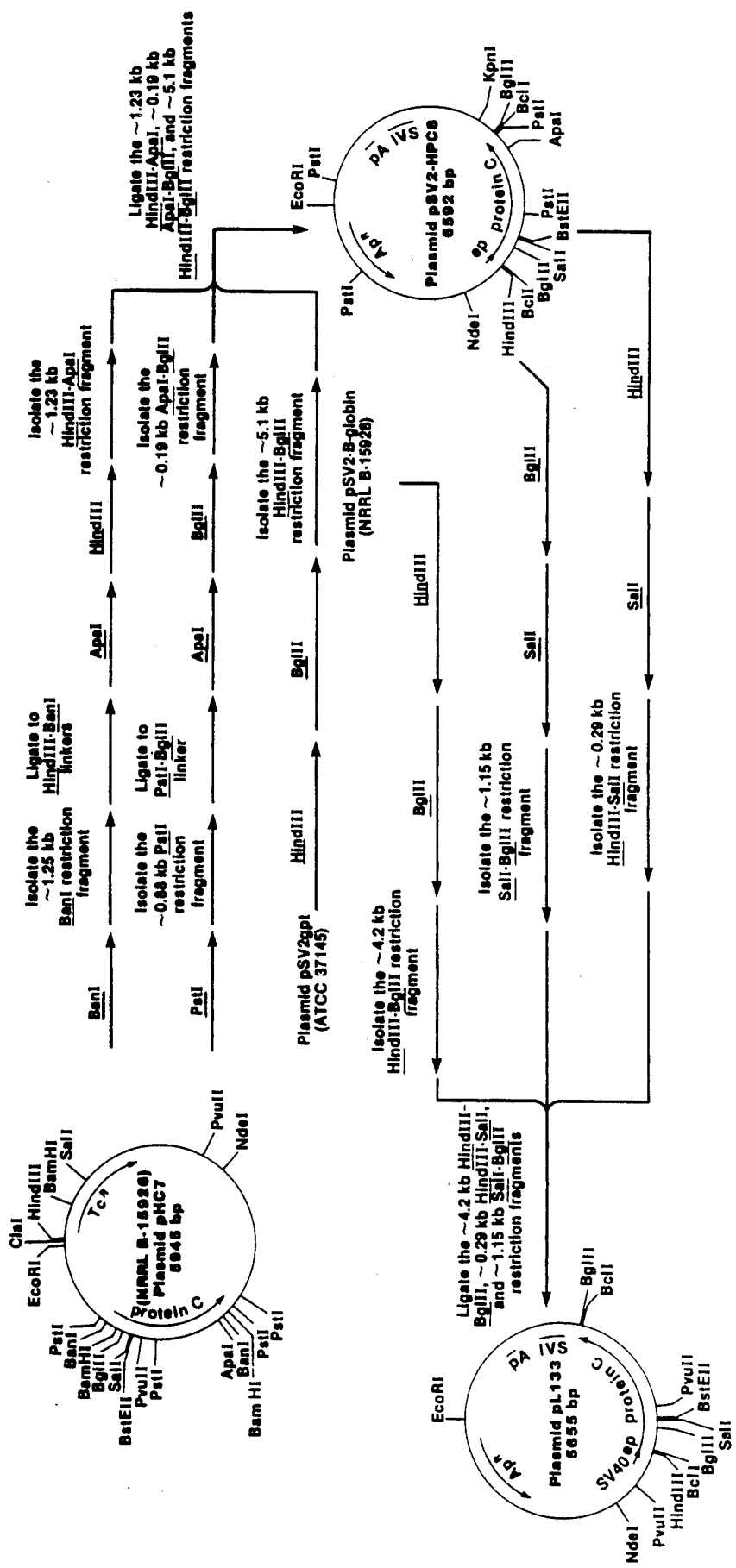
FIG. 2 schematically illustrates the construction of plasmid pL133, a starting material used in the construction of plasmid pLPC.

The ~1 mg of plasmid pHC7 DNA obtained by this procedure was suspended in 1 ml of TE buffer (10 mM Tris-HCl, pH=7.6, and 0.1 mM EDTA) and stored at −20° C. A restriction site and function map of plasmid pHC7 is presented in FIG. 2 of the accompanying drawings.

About 7 μg (7 μl) of plasmid pHC7 DNA were added to 25 μl of 10X Core buffer TM (Core buffer TM, BRL, is 500 mM Tris-HCl, pH=8.0; 500 mM NaCl; and 100 mM MgCl₂), 198 μl of H₂O, and 12 μl of restriction enzyme SstI (~60 units, Bethesda Research Laboratories (BRL), Gaithersburg, MD 20877; all enzymes referred to in these Examples are available, unless otherwise indicated, from BRL or New England Biolabs (NEB), Beverly, MA 01915-9990, and are used in substantial accordance with the manufacturer's recommendations), and 8 μl (80 units) of restriction enzyme SalI. The reaction mixture was incubated at 37° C. for four hours; then, the SstI-SalI digested plasmid pHC7 DNA was extracted first with phenol and then with chloroform, collected by precipitation with ethanol and centrifugation, and finally suspended in 15 μl of TE/10 buffer (10 mM Tris-base, pH=7.6, and 0.1 mM EDTA) buffer.

The reaction mixture was then electrophoresed on an ~0.6% low-gelling-temperature agarose (FMC Corporation, Marine Colloids Division, Rockland, Maine 04841) gel for 2-3 hours at ~130 V and ~65 mA in Tris-Acetate buffer. The gel was stained in a dilute solution of ethidium bromide, and the band of DNA constituting the ~0.7 kb SstI-SalI restriction fragment, which was visualized with long-wave UV light, was cut from the gel in a small segment. The volume of the segment was determined by weight and density of the segment, and four volumes of TE containing 0.25 M NaCl were added to the tube containing the segment. The segment was then melted by incubation at 72° C. About 0.5 μg of the ~0.7 kb SstI-SalI restriction fragment of plasmid pHC7 was obtained in a volume of about 400 μl. Further purification of the DNA was obtained by passing the solution of DNA through a NACS-prepac ® column (BRL) in accordance with the manufacturer's recommendations; the purified fragment was resuspended in 15 μl of deionized water.

B. Construction of Recombinant Phage and Removal of the Activation Peptide-encoding DNA by Site-Specific Mutagenesis About 1 μg of phage M13mp18 (obtained from New England Biolabs) RF (replicative form) DNA was digested with restriction enzymes SstI and SalI in substantial accordance with the procedure described in Example 1A. The reaction was stopped by extracting the reaction mixture with phenol and then chloroform; then, the DNA was precipitated, collected by centrifugation, and resuspended in about 15 μl of TE buffer. The two fragments resulting from the digestion were separated on an ~0.6% low-gelling-temperature agarose gel, and the larger fragment was cut out from the gel and purified as described in Example 1A.

About 0.1 μg (in 7 μl of H₂O) of the ~0.7 kb SstI-SalI restriction fragment of plasmid pHC7 was added to 5 μl of the SstI-SalI-digested M13mp18 RF DNA together with 2 μl of 10X ligase buffer (0.5 M Tris-HCl, pH=7.8; 60 mM MgCl₂; and 0.2 M dithiothreitol (DTT)), 2 μl of 1 mg/ml BSA, 1 μl of 25 mM ATP, 1 μl (~400 units) of T4 DNA ligase (NEB), and 2 μl of H₂O. The ligation reaction was incubated at 25° C. overnight; the ligated DNA constituted the desired phage M13mp18-HE1 DNA in double-stranded form.

About 300 μl of an overnight culture of *E. coli* K12 JM101 (New England Biolabs) were used to inoculate 30 ml of 2X TY broth (TY broth is 10 g/L tryptone, 10 g/L NaCl, and 5 g/L yeast extract), and the resulting culture was incubated at 37° C. with aeration until the O.D.₆₀₀ was ~0.5. The culture was chilled for 10 minutes in an ice-water bath, collected by centrifugation, and resuspended in 15 ml of cold, 10 mM NaCl. The cells were again collected by centrifugation and then resuspended in 15 ml of cold, 30 mM CaCl₂. The cells were placed on ice for 20 minutes and collected by centrifugation. The cells were resuspended in 1.5 ml of cold, 30 mM CaCl₂; a 200 μl aliquot of the cells was removed, added to 9 μl of the ligated DNA prepared above, and incubated on ice for about 30 minutes. The cell-DNA mixture was then incubated at 42° C. for 2 minutes and then added to 3 ml of top agar (TY broth with 0.5% agar kept molten at 45° C.) that also contained 50 μl of 2% X-Gal ("X-Gal" is 5-Bromo-4-chloro-3-indolyl-β-D-galactopyranoside), 50 μl of 100 mM IPTG ("IPTG" is isopropyl β-D-thiogalactopyranoside), and 100 μl of *E. coli* K12 JM101 in logarithmic growth phase. The cell-top agar mixture was then plated on TY-agar plates, and the plates were incubated at 37° C. overnight.

The following morning, four clear plaques were individually used to inoculate 2 ml of 2X TY broth, and the resulting cultures were incubated at 37° C. with aeration for 6 hours. Then, the cultures were centrifuged, and 500 μl of the resulting supernatant (the cell pellets were used to prepare phage DNA for restriction enzyme analysis) were added to 500 μl cultures (O.D.₅₅₀=0.5) of *E. coli* K12 JM101 and 50 ml of 2X TY broth. These cultures were incubated overnight at 37° C. The phage RF DNA was isolated from the cell pellets using a scaled-down version of the procedure described in Example 1A, except that no antibiotic was used in the culture media, and the ultracentrifugation steps were replaced with phenol and chloroform extractions. Transformants containing phage M13mp18-HE1 DNA were identified by restriction enzyme analysis of their phage DNA.

The overnight cultures were centrifuged, and about 1 ml of a solution composed of 20% polyethylene glycol (PEG) 6000 and 2.5 mM NaCl was added per 5 ml of supernatant, which was then incubated at room temperature for 10 minutes. The mixture was centrifuged for 10 minutes at 10,000 r.p.m., and the resulting pellet, which contained single-stranded phage M13mp18-HE1 DNA, was resuspended in 500 μl of TES buffer (20 mM Tris-HCl, pH=7.5; 0.1 M EDTA; and 10 mM NaCl). The DNA solution was extracted first with chloroform, then twice with TE-saturated phenol, and then again with chloroform. The single-stranded DNA was then precipitated using NaOAc and ethanol, centrifuged, and, after the pellet was washed with 70% ethanol and dried, the resulting pellet was dissolved in 80 μl of H₂O. This phage preparation was used in the next step, the site-specific mutagenesis, to remove the activation peptide-encoding DNA.

The single-stranded DNA fragment used in the mutagenesis to remove the activation peptide-encoding DNA was synthesized on an automated DNA synthesizer and is depicted below:
5'-GCGCAGTCACCTGAAACGACTCATT-GATGGGAAGATGA-3'.

About 30 picomoles (1 μl) of the single-stranded DNA fragment depicted above (the "mutagenic oligonucleotide") and 1.5 μl (7.5 picomoles) of the M13 universal primer (marketed by Boehringer-Mannheim Biochemicals (BMB), 7941 Castleway Drive, P.O. Box 50816, Indianapolis, IN 46250) were individually treated with 5 units (Pharmacia, P-L Biochemicals, Inc., 800 Centennial Avenue, Piscataway, NJ 08854) of T4 polynucleotide kinase in 10 μl of 1X kinase buffer (100 mM Tris-HCl, pH=8.3; 100 mM DDT; and 100 mM MgCl₂) containing 1 μl of 1 mM ATP for 30 minutes at 37° C., followed by a 10 minute, 65° C. incubation and subsequent freezing. The kinase-treated DNAs were used in the mutagenesis procedure described below.

In the first step of the mutagenesis procedure, the mutagenic oligonucleotide and the M13 universal primer were annealed to the single-stranded phage DNA. The annealing reaction was carried out by adding 300 nanograms (0.5 μl) of single-stranded phage M13mp18-HE1 to 1 picomole (1.2 μl) of the universal primer, 1 picomole (0.3 μl) of the mutagenic oligonucleotide, 2 μl of 10X annealing buffer (100 mM Tris-HCl, pH=7.5; 1 mM EDTA; and 500 mM NaCl), and 16 μl of H₂O, incubating the mixture at 80° C. for 2 minutes and then at 50° C. for 5 minutes, and, finally, allowing the mixture to cool to room temperature.

Once the oligonucleotides were annealed, the phage DNA was made double-stranded by extending the primers with DNA polymerase. The extension reaction was carried out by adding 3 μl of 10X extension buffer (500 mM Tris-HCl, pH=8; 1 mM EDTA; and 120 mM MgCl₂); 3 μl of 10X ligase buffer; 1.5 μl of 0.2 mM DTT; 3 μl of dNTP mix (0.5 mM in each dNTP); 1.2 μl of 25 mM ATP; 0.5 μl of Klenow enzyme (5 U/μl, BMB); 1 μl of T4 DNA ligase (400 U, NEB); and 19.8 μl of H2O to the mixture of annealed DNA. The extension reaction was incubated at room temperature for 30 minutes, then at 37° C. for 4 hours, and then overnight at 4° C.

The reaction was stopped by a phenol-chloroform extraction and precipitation of the DNA with ethanol and sodium acetate (NaOAc). The DNA was collected by centrifugation and resuspended in 40 μl of S1 buffer (0.3 M NaCl; 0.03 M NaOAc, pH=4.5; and 0.3 mM ZnCl2) were then added to the solution of DNA. The S1 treatment described below has been reported to be beneficial in site-specific mutagenesis procedures. However, the present inventors found no significant advantage in the S1 treatment and, in the construction protocols described in subsequent Examples herein, omitted the S1 treatment entirely.

The solution of DNA was split equally into two tubes, and to one of the tubes, 100 units (BMB) of S1 nuclease were added. The S1 reaction was incubated at room temperature for 5 minutes and stopped by extracting the reaction mixture once with TE-saturated phenol-chloroform (50:50). The DNA was precipitated from the reaction mixture and from the non-S1-treated sample with NaOAc and ethanol.

The DNA pellets were resuspended in 60 μl of H2O and used to transform *E. coli* K12 JM101 in accordance with the procedure used during the construction of phage M13mp18-HE1, except that no IPTG or X-Gal was added to the plates. The mutants were screened for by using a small portion of the mutagenic oligonucleotide, 5'-TGAAACGACTCATTGA-3' (radioactively labelled), as a probe in plaque and dot-blot hybridizations. Several plaques that appeared positive from the hybridizations were picked and individually inoculated into 2 ml of a culture of *E. coli* K12 JM101 in logarithmic growth phase. These cultures were incubated at 37° C. with aeration for about 6 hours, when they were then used to prepare single-stranded DNA as described above for phage M13mp18-HE1.

The single-stranded DNA was sequenced using the dideoxy-sequencing method (J.H. Smith, 1980, Methods in Enzymology 65:560–580). Several phage were identified with the desired mutation. Phage in which the coding sequence for the activation peptide was deleted were designated phage M13mp18-HE2. The mutation in phage M13mp18-HE2 causes a decrease in size of 36 bp with respect to the natural coding sequence, a difference that can be used to facilitate identification of DNA that contains the mutated region. The RF form of phage M13mp18-HE2 was prepared for use in subsequent constructions.

C. Final Construction of Plasmid pLAPC From Phage M13mp18-HE2 and Plasmid pLPC

The mutagenized SstI-SalI (~0.7 kb) restriction fragment of the RF form of phage M13mp18-HE2 was cut from the phage and isolated in substantial accordance with the procedure of Example 1A. However, the ~100 μl of solution containing ~0.1 μg of the desired ~0.7 kb fragment in a 1:2 dilution of low-gelling agarose were not passed through any purification column but were used directly in the ligation to produce plasmid pLAPC, described below.

Three DNA fragments were ligated together to form plasmid pLAPC: the ~0.7 kb SstI-SalI restriction fragment of phage M13mp18-HE2, described above, and two DNA fragments from plasmid pLPC. The construction protocol for plasmid pLPC is described in Example 2. A restriction site and function map of plasmid pLPC is presented in FIG. 1 of the accompanying drawings. Because of the positioning of SalI, SstI, and EcoRI restriction enzyme recognition sites on plasmid pLPC, the desired EcoRI-SalI and EcoRI-SstI restriction fragments had to be prepared in two separate digestions.

To prepare the EcoRI-SstI fragment, about 40 μg of plasmid pLPC in 25 μl of H2O were added to 10 μl of 1 mg/ml BSA, 10 μl of 10X Core buffer TM (BRL), 5 μl of restriction enzyme EcoRI (50 U, BRL), 5 μl of restriction enzyme SstI (25 U, BRL), and 45 μl of H2O, and the resulting reaction was incubated at 37° C. for 1.5 hours. The SstI-EcoRI-digested plasmid pLPC DNA was collected by precipitation with ethanol and centrifugation. The SstI-EcoRI-digested DNA was resuspended in water and then loaded onto an ~0.6% low-gelling-temperature agarose gel to separate the DNA fragments by electrophoresis.

To prepare the EcoRI-SalI fragment, about 15 μg of plasmid pLPC in 9 μl of H2O were first treated with restriction enzyme ApaI to eliminate contamination by similarly-sized restriction fragments. About 10 μl of 10X ApaI buffer (60 mM NaCl; 60 mM Tris-HCl, pH=7.4; 60 mM MgCl2; and 60 mM DTT), 10 μl of 1 mg/ml BSA, 69 μl of H2O, and 2 μl of restriction enzyme ApaI (50 U, NEB) were added to the solution of plasmid pLPC DNA, and the resulting reaction was incubated at 37° C. for one hour. Then, 15 μl of 2 M NaCl, 69 μl of H2O, 8 μl of restriction enzyme SalI (NEB), and 8 μl of restriction enzyme EcoRI (NEB), were added to the solution of ApaI-digested plasmid pLPC DNA, and the resulting reaction was incubated at 37° C. for one hour. The ApaI-SalI-EcoRI-digested plasmid pLPC DNA was extracted first with phenol and then with chloroform, then collected by precipitation with ethanol and centrifugation, and finally resuspended in 25 μl of H2O. The DNA was then loaded onto an ~0.6% low-gelling-temperature agarose gel and the DNA fragments separated by electrophoresis.

The ~3.76 kb EcoRI-SalI and the ~2.0 kb EcoRI-SstI restriction fragments were cut from the gels and the gel fragments melted after adding equal volumes of 10 mM Tris-HCl, pH=7.6, as described in Example 1A. About 2 μg of the ~3.76 kb EcoRI-SalI restriction fragment of plasmid pLPC were thus obtained in ~200 μl of 10 mM Tris-HCl, pH=7.6, which also contained the melted agarose. About 2 μg of the ~2.0 kb EcoRI-SalI restriction fragment of plasmid pLPC were obtained in a separate ~200 μl of 10 mM Tris-HCl, pH=7.6, containing agarose.

About 12.5 μl of each solution of the two purified restriction fragments (the ~3.76 kb EcoRI-SalI restriction fragment of plasmid pLPC and the ~2.0 kb EcoRI-SstI restriction fragment of plasmid pLPC) were added to 20 μl of the ~0.7 kb SstI-SalI restriction fragment of phage M13mp18-HE2, 10 μl of 1 mg/ml BSA, 10 μl of 10 mM ATP, 10 μl of 10X ligase buffer, 2 μl (~800 U, NEB) of T4 DNA ligase, and 23 μl of H2O, and the resulting ligation reaction was incubated at 15° C. overnight. The ligated DNA constituted the desired plasmid pLAPC. Plasmid pLAPC only differs from plasmid pLPC (FIG. 1) in the deletion of the activation peptide-encoding DNA.

To check plasmid structure and obtain large amounts of plasmid pLAPC for eukaryotic cell transformation and further constructions, the ligated DNA containing plasmid pLAPC was used to transform *E. coli* K12 RV308, available from the NRRL under the accession number NRRL B-15624.

A 50 ml culture of *E. coli* K12 RV308 in L broth was grown to an optical density (O.D.) at 590 nm of ~0.6. The culture was chilled on ice for ten minutes, and the cells were collected by centrifugation. The cell pellet was resuspended in 25 ml of cold, 10 mM NaCl. The cells were again pelleted by centrifugation, and the pellet was resuspended in 25 ml of cold, 30 mM $CaCl_2$ and incubated on ice for 30 minutes. The cells were again collected by centrifugation and resuspended in 2.5 ml of cold, 30 mM $CaCl_2$.

Two hundred μl of this cell suspension were mixed with the ligated DNA containing plasmid pLAPC and incubated on ice for 60 minutes. The mixture was then incubated at 42° C. for 2 minutes, followed by a 10 minute incubation at room temperature. About 10 ml of 2X TY broth were added to the cell-DNA mixture, and then the cells were incubated in an air-shaker incubator in a 125 ml flask at 37° C. for two hours.

Aliquots of the cell mixture were plated on TY-agar (TY broth with 15 g/l agar) plates containing 100 μg/ml ampicillin, and the plates were then incubated at 37° C. overnight. *E. coli* K12 RV308/pLAPC transformants were verified by restriction enzyme analysis of their plasmid DNA. Plasmid DNA was obtained from the *E. coli* K12 RV308/pLAPC transformants in substantial accordance with the teaching of Example 1A, except that 50 μg/ml of ampicillin, and not tetracycline, was used as the selective agent.

EXAMPLE 2

The Construction of Plasmid pLPC

Plasmid pLPC was used as an intermediate vector in the construction of plasmid pLAPC (see Example 1C). Plasmid pLPC comprises a segment of DNA that encodes the BK virus enhancer and the adenovirus 2 late promoter positioned to drive expression of human protein C. The construction protocol for plasmid pLAPC essentially results in the replacement of the human protein C coding sequence on plasmid pLPC with another protein C coding sequence from which the activation peptide-encoding DNA has been removed.

The BK enhancer/adenovirus late promoter expression control sequences on plasmids pLPC and pLAPC are the subject matter of U.S. Patent Application Ser. No. 06/849,999, filed Apr. 9, 1986, attorney docket number X-6606. U.S. Patent Application Ser. No. 06/849,999 discloses that the expression control sequence of plasmid pLPC (and thus pLAPC) is greatly stimulated in its activity by the presence of an immediate early gene product of a large DNA virus, i.e., the E1A gene product of adenovirus.

Figure 1C:
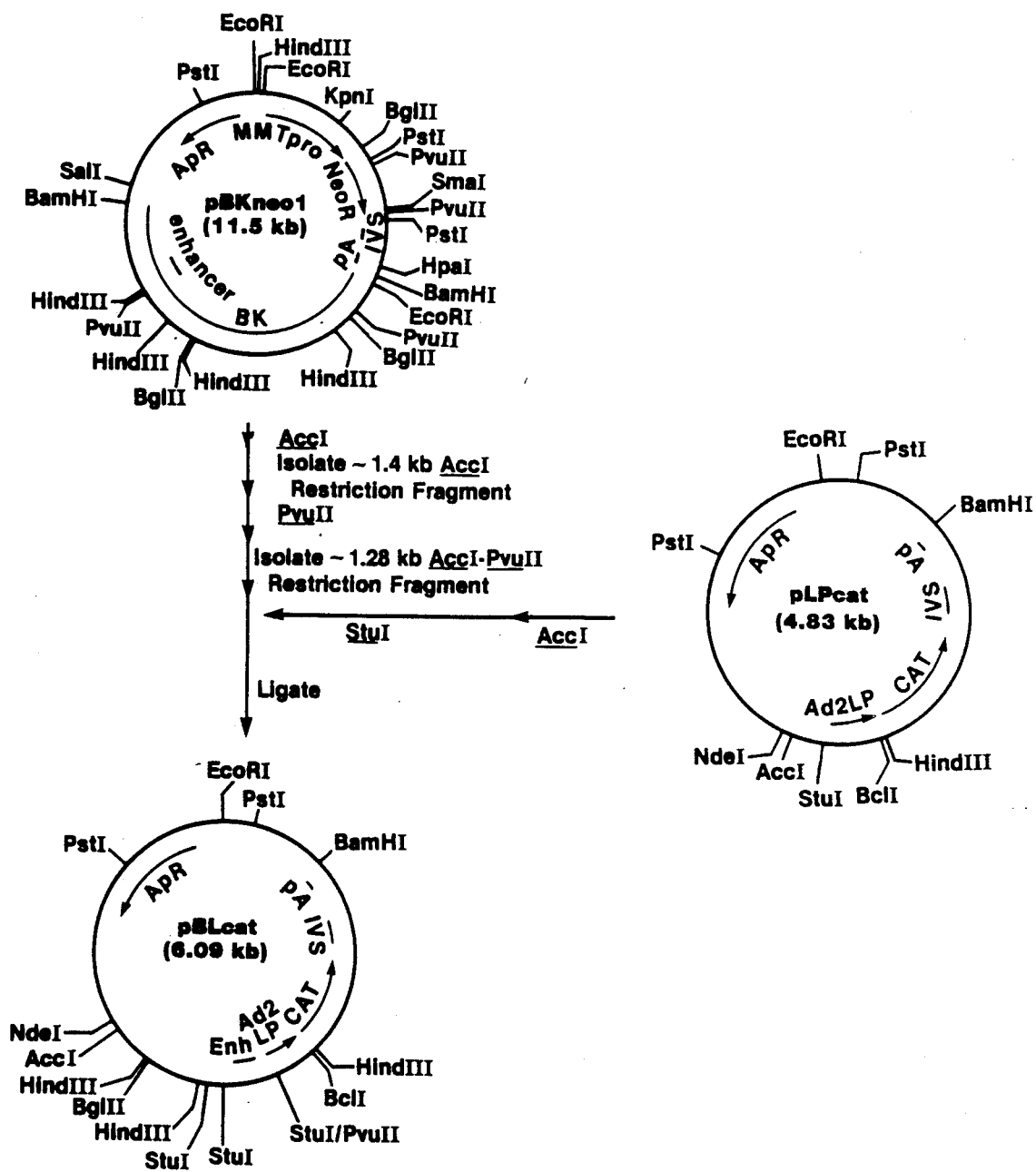
Figure 1D:
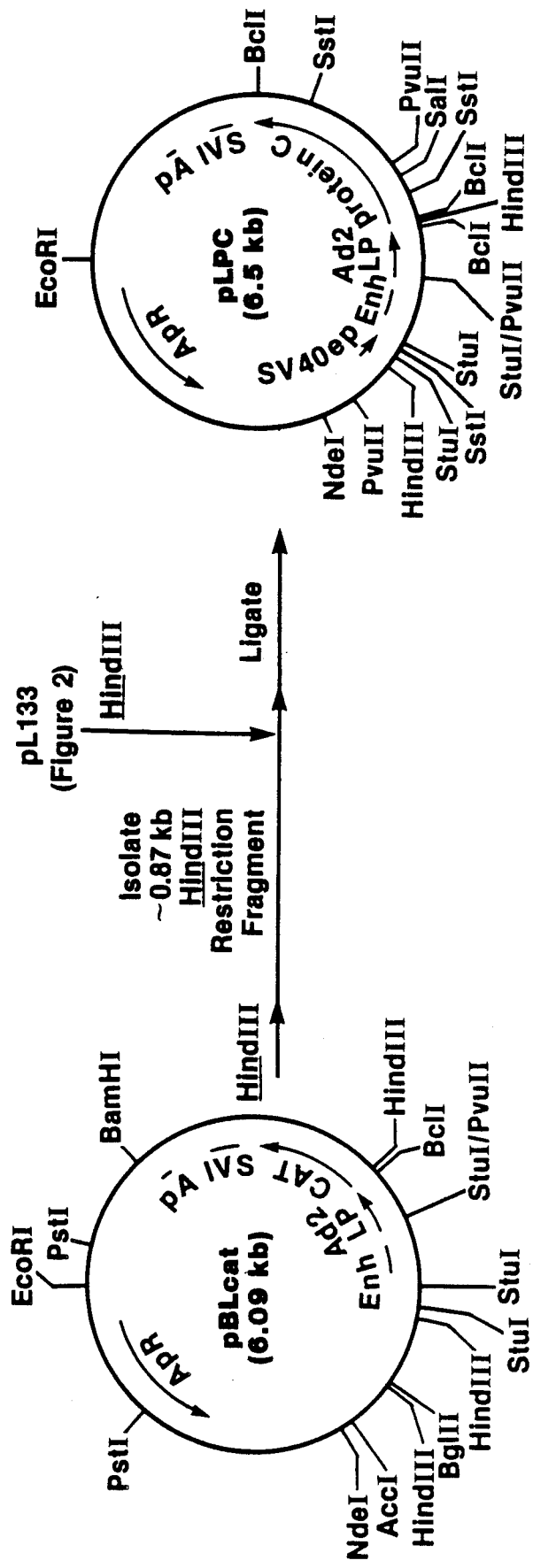

The construction protocol for plasmid pLPC is set forth below. The entire construction protocol for plasmid pLPC is schematically illustrated in FIG. 1 of the accompanying drawings. In brief, Example 2A describes the isolation of BK virus DNA, from which the BK enhancer can be obtained. Example 2B sets forth the construction protocol for plasmid pBKneol, a plasmid resulting from the insertion of the BK enhancer into plasmid pdBPV-MMTneo. Example 2C teaches the construction protocol for plasmid pLPcat, a plasmid resulting from the insertion of the adenovirus 2 late promoter into plasmid pSV2cat. Example 2D teaches the construction protocol for plasmid pBLcat, a plasmid that contains the BK enhancer positioned to stimulate the activity of the adenovirus late promoter. Example 2E describes the construction protocol for plasmid pL133, a protein C expression vector, beginning with starting material plasmid pHC7 and proceeding through the construction of intermediate plasmid pSV2-HPC8 and then the final construction of plasmid pL133. Finally, Example 2F teaches the construction protocol for plasmid pLPC, which comprises the BK enhancer-/adenovirus late promoter expression control sequence of plasmid pBLcat inserted into plasmid pL133 to drive expression of human protein C.

A. Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, NY 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, VA 22101, under catalogue number 0–100 or from M.A. Bioproducts under catalogue number 70–151.

About five 75 $mm^2$ polystyrene flasks comprising confluent monolayers of about $10^5$ PHEK cells are used to prepare the virus. About 1 ml of BK virus at a titer of $10^5$ pfu/ml is added to each flask, which is then incubated at 37° C. for one hour, and then, fresh culture medium (Dulbecco's Modified Eagle Medium, Gibco, Grand Island, NY 14072, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000Xg. The virus in 1 liter of supernatant fluid is precipitated and collected by the addition of 100 g of PEG-6000, incubation of the solution for 24 hours at 4° C., and centrifugation at 5000Xg for 20 minutes. The pellet is dissolved in 0.1X SSC buffer (1XSSC=0.15 M NaCl and 0.015 M NaCitrate, pH=7) at 1/100th of the original volume. The virus suspension is layered onto a 15 ml solution of saturated KBr in a tube, which is centrifuged at 75,000Xg for 3 hours. Two bands are evident in the KBr solution after centrifugation. The lower band, which contains the complete virion, is collected and desalted on a Sephadex ® G-50 column (Sigma Chemical Co., St. Louis, MO 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase ® (Sigma) protease is added to a concentration of 100 μg/ml, and the solution is incubated at 37° C. for 2 hours. Cesium chloride is then added to the solution to a density of 1.56 g/ml, and ethidium bromide is added to the solution to a final concentration of 100 μg/ml. The solution is centrifuged in a Sorvall 865 rotor (DuPont Co., Newton, CT 06470) or similar vertical rotor at 260,000Xg for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15 M, adding two volumes of ethanol, incubating the solution at −70° C. for at least 2 hours, and centrifuging the solution at 12,000Xg for 10 minutes. The resulting pellet of BK virus DNA is suspended in TE buffer at a concentration of 1 mg/ml. A restriction site and function map of BK virus is presented in FIG. 1 of the accompanying drawings.

B. Construction of Plasmid pBKneol

*E. coli* K12 HB101/pdBPV-MMTneo cells are obtained in lyophilized form from the American Type Culture Collection under the accession number ATCC 37224. The lyophilized cells are plated on L-agar plates containing 100 μg/ml ampicillin and incubated at 37° C. to obtain single colony isolates.

One liter of L broth (10 g tryptone, 10 g NaCl, and 5 g yeast extract per liter) containing 50 μg/ml ampicillin was inoculated with a colony of *E. coli* K12 HB101/pdBPV-MMTneo and incubated in an air-shaker at 37° C. until the $O.D._{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue. Plasmid pdBPV-MMTneo DNA was then prepared from the culture in substantial accordance with the procedure described in Example 1A.

The ~1 mg of plasmid pdBPV-MMTneo DNA obtained by this procedure was suspended in 1 ml of TE buffer and stored at −20° C. The plasmid isolation procedure described in Example 1A is generally used when large amounts of very pure plasmid DNA are desired. The procedure can be modified to obtain rapidly a smaller, less pure amount of DNA, such as is needed when screening transformants for the presence of a given plasmid, by using only about 5 ml of cultured cells, lysing the cells in an appropriately scaled-down amount of lysis buffer, and replacing the centrifugation steps with phenol and chloroform extractions.

About 5 μg (5 μl) of the plasmid pdBPV-MMTneo DNA prepared as described above and five μg (5 μl) of the BK virus DNA prepared as described above were each digested at 37° C. for 2 hours in a solution containing 2 μl of 10X BamHI buffer (1.5 M NaCl; 60 mM Tris-HCl, pH=7.9; 60 mM $MgCl_2$; and 1 mg/ml BSA), 1 μl (~10 units) of restriction enzyme BamHI, and 7 μl of $H_2O$. The reaction was stopped by an extraction with an equal volume of phenol, followed by two extractions with chloroform. Each BamHI-digested DNA was then precipitated, collected by centrifugation, and resuspended in 5 μl of $H_2O$.

About 1 μl of 10X ligase buffer was added to a mixture of BamHI-digested plasmid pdBPV-MMTneo (1 μl) and BamHI-digested BK virus DNA (1 μl). After 1 μl (~5 units) of T4 DNA ligase and 6 μl of $H_2O$ were added to the mixture of DNA, the resulting reaction was incubated at 16° C. overnight. The ligated DNA constituted the desired plasmids pBKneoI and pBKneo2, which differ only with respect to the orientation of the BK virus DNA. A restriction site and function map of plasmid pBKneol is presented in FIG. 1 of the accompanying drawings.

*E. coli* K12 HB101 cells are available in lyophilized form from the Northern Regional Research Laboratory under the accession number NRRL B-15626. A 50 ml culture of *E. coli* K12 HB101 in L broth was grown to an optical density at 650 nanometers ($O.D._{650}$) of approximately 0.4 absorbance units. The culture was chilled on ice for ten minutes, and the cells were collected by centrifugation. The cell pellet was resuspended in 25 ml of cold 100 mM $MgCl_2$ and incubated on ice for 25 minutes. The cells were once again pelleted by centrifugation, and the pellet was resuspended in 2.5 ml of cold 100 mM $CaCl_2$ and incubated for 30 minutes on ice. After the incubation, the cells are competent for the uptake of transforming DNA.

Two hundred μl of this cell suspension were mixed with the ligated DNA prepared above and incubated on ice for 30 minutes. At the end of this period, the cells were placed in a water bath at 42° C. for 2 minutes and then returned to the ice for an additional 10 minutes. The cells were collected by centrifugation and resuspended in one ml of L broth and incubated at 37° C. for 1 hour. The transformed cells were plated on L-agar plates containing 100 μg/ml ampicillin. *E. coli* K12 HB101/pBKneol and *E. coli* K12/pBKneo2 transformants were identified by their ampicillin-resistant phenotype and by restriction enzyme analysis of their plasmid DNA. A restriction site and function map of plasmid pBKneol is presented in FIG. 1, Part A, of the accompanying drawings.

C. Construction of Plasmid pLPcat, an Intermediate Plasmid Used in the Construction of Plasmid pBLcat The virion DNA of adenovirus 2 (Ad2) is a double-stranded linear molecule about 35.94 kb in size. The Ad2 late promoter can be isolated on an ~0.32 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL) are dissolved in 80 μl of $H_2O$ and 10 μl of 10X BalI buffer (100 mM Tris-HCl, pH=7.6; 120 mM $MgCl_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, NH 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1 M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25 M, and then three volumes of cold, absolute ethanol are added to the solution. The resulting solution is mixed and placed at −70° C. for 10–20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of H2O and 2 μl of 10X AccI buffer (60 mM NaCl; 60 mM Tris-HCl, pH=7.5; 60 mM MgCl2; 60 mM DTT; and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H2O and 2 μl of 10X PvuII buffer (600 mM NaCl; 60 mM Tris-HCl, pH=7.5; 60 mM MgCl2; 60 mM DTT; and 1 mg/ml BSA). After the addition of about 2 μl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH4OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H2O.

To convert the AccI-PvuII restriction fragment to an AccI-BclI restriction fragment, BclI linkers were ligated to the ~0.32 AccI-PvuII restriction fragment. Because the BclI linkers were blunt-ended, the linkers only attached to the PvuII end of the restriction fragment. The BclI linkers (New England Biolabs), which had the following sequence:

were kinased and prepared for ligation by the following procedure. Four μl of linkers (~2 μg) were dissolved in 20.15 μl of H2O and 5 μl of 10X kinase buffer (500 mM Tris-HCl, pH=7.6 and 100 mM MgCl2), incubated at 90° C. for two minutes, and then cooled to room temperature. Five μl of γ-32P-ATP (~20 μCi), 2.5 μl of 1 M DTT, and 5 μl of polynucleotide kinase (~10 units) were added to the mixture, which was then incubated at 37° C. for 30 minutes. Then, 3.35 μl of 0.01 M ATP and 5 μl of kinase were added, and the reaction was continued for another 30 minutes at 37° C. The radioactive ATP aids in determining whether the linkers have ligated to the target DNA.

About 0.25 μg (in 0.5 μl) of the kinased BclI linkers was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

E. coli K12 HB101/pSV2cat cells are obtained in lyophilized form from the ATCC under the accession number ATCC 37155, and plasmid pSV2cat DNA was isolated from the cells in substantial accordance with the procedure of Example 1A, except that ampicillin, at 50 μg/ml, was used in place of tetracycline. A restriction site and function map of plasmid pSV2cat is presented in FIG. 1, Part B, of the accompanying drawings. About 1 mg of plasmid pSV2cat DNA is obtained and dissolved in 1 ml of TE buffer. About 3 μg (3 μl) of the plasmid pSV2cat DNA were added to 2 μl of 10X AccI buffer and 16 μl of H2O, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 μl of 10X StuI buffer (1.0M NaCl; 100 mM Tris-HCl, pH=8.0; 100 mM MgCl2; 60 mM DTT; and 1 mg/ml BSA), 5 μl of H2O, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

About 4 μl of the AccI-StuI-digested plasmid pSV2cat DNA were mixed with about 7 μl of the ~0.32 kb AccI-PvuII (with BclI linkers attached) restriction fragment of Ad2, and after the addition of 3 μl of 10X ligase buffer, 15 μl of H2O, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 1, Part B, of the accompanying drawings.

The ligated DNA was used to transform E. coli K12 HB101 cells in substantial accordance with the procedure of Example 2B. The transformed cells were plated on L-agar plates containing 50 μg/ml ampicillin; restriction enzyme analysis of plasmid DNA was used to identify the E. coli K12 HB101/pLPcat transformants.

Plasmid pLPcat DNA was isolated from the transformants for use in subsequent constructions in substantial accordance with the plasmid isolation procedure described in Example 1A, except that ampicillin was used as the selective agent in place of tetracycline.

D. Construction of Plasmid pBLcat

About 88 μg of plasmid pBKneol DNA in 50 μl of TE buffer were added to 7.5 μl of 10X AccI buffer, 30 μl of H$_2$O, and 15 μl (about 75 units) of restriction enzyme AccI, and the resulting reaction was incubated at 37° C. for 2 hours. The AccI-digested plasmid pBKneol DNA was loaded on an agarose gel, and the ~1.4 kb fragment that contains the BK enhancer was separated from the other digestion products. The ~1.4 kb AccI restriction fragment was then isolated from the gel and purified. About 5 μg of the fragment were resuspended in 5 μl of 10X PvuII buffer, 45 μl of H$_2$O, and 5 μl (about 25 units) of restriction enzyme PvuII, and the resulting reaction was incubated at 37° C. for 2 hours. The PvuII-digested DNA was then isolated, purified, and prepared for ligation. About 2 μg of the desired ~1.28 kb AccI-PvuII fragment were obtained and dissolved in 5 μl of TE buffer.

About 1 μg of plasmid pLPcat DNA was dissolved in 5 μl of 10X AccI buffer and 40 μl of H$_2$O. About 5 μl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10X StuI buffer, 40 μl of H$_2$O, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

The 5 μl of ~4.81 kb AccI-StuI restriction fragment of plasmid pLPcat were added to 5 μl of ~1.28 kb AccI-PvuII restriction fragment of plasmid pBKneol. After the addition of 3 pl of 10X ligase buffer, 15 μl of H$_2$O, and 2 μl (about 10 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 1, Part C, of the accompanying drawings.

The ligated DNA was used to transform *E. coli* K12 HB101 cells in substantial accordance with the procedure described in Example 2B. *E. coli* K12 HB101/pBLcat transformants were identified by restriction enzyme analysis of their plasmid DNA. Plasmid pBLcat DNA was prepared for use in subsequent constructions in substantial accordance with the procedure of Example 1A, except that ampicillin was used as the selective agent in place of tetracycline.

E. Construction of Plasmid pL133

Plasmid pL133 is a human protein C expression vector disclosed and claimed in U.S. Patent Application Ser. No. 06/699,967, filed Feb. 8, 1985, attorney docket No. X-6737. As described below, plasmid pL133 can be constructed using starting vector plasmids pSV2gpt and pHC7 (the preparation of plasmid pHC7 is described above in Example 1A) to construct intermediate vector plasmid pSV2-HPC8, which is then combined with plasmid pSV2-β-globin to yield plasmid pL133. The construction protocol for plasmid pL133 is described in detail, below, and schematically illustrated in FIG. 2 of the accompanying drawings.

Fifty μl (~50 μg) of plasmid pHC7 DNA were mixed with 5 μl (~50 units) of restriction enzyme BanI, 10 μl of 10X BanI reaction buffer (1.5 M NaCl; 60 mM Tris-HCl, pH=7.9; 60 mM MgCl$_2$; and 1 mg/ml BSA), and 35 μl of H$_2$O and incubated until the digestion was complete. The BanI-digested plasmid pHC7 DNA was then electrophoresed on a 3.5% polyacrylamide gel (29:1, acrylamide:bis-acrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM NH$_4$OAc, 10 mM MgOAc, 1 mM EDTA, 1% SDS, and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8. The DNA fragments used in the construction of the linker were synthesized either by using a Systec 1450A DNA Synthesizer (Systec Inc., 3816 Chandler Drive, Minneapolis, MN) or an ABS 380A DNA Synthesizer (Applied Biosystems, Inc., 850 Lincoln Centre Drive, Foster City, CA 94404). Many DNA synthesizing instruments are known in the art and can be used to make the fragments. In addition, the fragments can also be conventionally prepared in substantial accordance with the procedures of Itakura et al., 1977, Science, 198:1056 and Crea et al., 1978, Proc. Nat. Acad. Sci. USA, 75:5765.

Five hundred picomoles of each single strand of the linker were kinased in 20 μl of reaction buffer, which contained 15 units (~0.5 μl) T4 polynucleotide kinase, 2 μl 10X ligase buffer, 10 μl of 500 μM ATP, and 7.5 μl of H$_2$O. The kinase reaction was incubated at 37° C. for 30 minutes, and the reaction was terminated by incubation at 100° C. for 10 minutes. To ensure complete kination, the reaction was chilled on ice, 2 μl of 0.2 M dithiothreitol, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The linker constructed had the following structure:

The linker was stored at −20° C. until use.

The ∼8 μg of ∼1.25 kb BanI fragment were added to and mixed with the ∼50 μl of linker (∼500 picomoles), 1 μl of T4 DNA ligase (∼5 units), 10 μl of 10X ligase buffer, and 29 μl of H2O, and the resulting ligation reaction was incubated at 4° C. overnight. The ligation reaction was stopped by a 10 minute incubation at 65° C. The DNA was pelleted by adding NaOAc to a final concentration of 0.3 M, adding 2 volumes of ethanol, chilling in a dry ice-ethanol bath, and then centrifuging the solution.

The DNA pellet was dissolved in 10 μl of 10X ApaI reaction buffer (60 mM NaCl; 60 mM Tris-HCl, pH=7.4; 60 mM MgCl2; and 60 mM 2-mercaptoethanol), 5 μl (∼50 units) of restriction enzyme ApaI, and 85 μl of H2O, and the reaction was placed at 37° C. for two hours. The reaction was then stopped and the DNA pelleted as above. The DNA pellet was dissolved in 10 μl of 10X HindIII reaction buffer, 5 μl (∼50 units) of restriction enzyme HindIII, and 85 μl of H2O, and the reaction was placed at 37° C. for two hours. After the HindIII digestion, the reaction mixture was loaded onto a 3.5% polyacrylamide gel, and the desired ∼1.23 kb HindIII-ApaI restriction fragment was isolated from the gel and purified. Approximately 5 μg of the desired fragment were obtained, suspended in 10 μl of TE buffer, and stored at −20° C.

Fifty μl (∼50 μg) of plasmid pHC7 DNA were mixed with 5 μl (∼50 units) of restriction enzyme PstI, 10 μl of 10X PstI reaction buffer (1.0 M NaCl; 100 mM Tris-HCl, pH=7.5; 100 mM MgCl2; and 1 mg/ml BSA), and 35 μl of H2O and incubated at 37° C. for two hours. The PstI-digested plasmid pHC7 DNA was then electrophoresed on a 3.5% polyacrylamide gel, and the desired ∼0.88 kb fragment was purified in substantial accordance with the procedure described above. Approximately 5 μg of the desired fragment were obtained, suspended in 10 μl of TE buffer, and stored at −20° C.

The ∼5 μg of ∼0.88 kb PstI fragment were added to and mixed with ∼50 μl of the following linker, which was constructed on an automated DNA synthesizer:

About 1 μl of T4 DNA ligase (∼10 units), 10 ∼1 10X ligase buffer, and 29 μl H2O were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10X ApaI reaction buffer, 5 μl (∼50 units) of restriction enzyme ApaI, and 85 μl of H2O, and the reaction was placed at 37° for two hours. The reaction was then stopped and the DNA pelleted once again. The DNA pellet was dissolved in 10 ∼1 10X BglII reaction buffer (1 M NaCl; 100 mM Tris-HCl, pH=7.4; 100 mM MgCl2; 100 mM 2-mercaptoethanol; and 1 mg/ml BSA), 5 μl (∼50 units) of restriction enzyme BglII, and 85 μl H2O, and the reaction was placed at 37° C. for two hours. After the BglII digestion, the reaction mixture was loaded onto a 3.5% polyacrylamide gel, and the desired ∼0.19 kb ApaI-BglII restriction fragment was isolated in substantial accordance with the procedure described above. Approximately 1 μg of the desired fragment was obtained, suspended in 10 μl of TE buffer, and stored at −20° C.

Approximately 10 μg of plasmid pSV2gpt DNA (ATCC 37145) were dissolved in 10 μl of 10X HindIII reaction buffer, 5 μl (∼50 units) of restriction enzyme HindIII, and 85 μl of H2O, and the reaction was placed at 37° C. for 2 hours. The reaction mixture was then made 0.25 M in NaOAc, and after the addition of two volumes of ethanol and incubation in a dry ice-ethanol bath, the DNA was pelleted by centrifugation. The DNA pellet was dissolved in 10 μl of 10X BglII buffer, 5 μl (∼50 units) of restriction enzyme BglII, and 85 μl of H2O, and the reaction was placed at 37° C. for two hours. After the BglII digestion, the reaction mixture was loaded onto a 1% agarose gel, and the fragments were separated by electrophoresis. The gel was stained with ethidium bromide and viewed under ultraviolet light, and the band containing the desired ∼5.1 kb HindIII-BglII fragment was cut from the gel and placed in dialysis tubing, and electrophoresis was continued until the DNA was out of the agarose. The buffer containing the DNA from the dialysis tubing was extracted with phenol and CHCl3, and then, the DNA was precipitated. The pellet was resuspended in 10 μl of TE buffer and constituted ∼5 μg of the desired ∼5.1 kb HindIII-BglII restriction fragment of plasmid pSV2gpt.

Two μl of the ∼1.23 kb HindIII-ApaI restriction fragment, 3 μl of the ∼0.19 kb ApaI-BglII fragment, and 2 μl of the ∼5.1 kb HindIII-BglII fragment were mixed together and then incubated with 10 μl of 10X ligase buffer, 1 μl of T4 DNA ligase (∼500 units), and 82 μl of H2O at 16° C. overnight. The ligated DNA constituted the desired plasmid pSV2-HPC8; a restriction site and function map of the plasmid is presented in FIG. 2 of the accompanying drawings.

E. coli K12 RR1 (NRRL B−15210) cells were made competent for transformation in substantial accordance with the procedure described for E. coli K12 HB101 in Example 2B. The ligated DNA prepared above was used to transform the cells, and aliquots of the transformation mix were plated on L-agar plates containing 100 μg/ml ampicillin. The plates were then incubated at 37° C. E. coli K12 RR1/pSV2-HPC8 transformants were verified by restriction enzyme analysis of their plasmid DNA. Plasmid pSV2-HPC8 DNA was prepared from the transformants in substantial accordance with the procedure of Example 1A, except that ampicillin, and not tetracycline, was used as the selective agent during culture of the cells.

Fifty μg of plasmid pSV2-HPC8 were dissolved in 10 μl of 10X HindIII reaction buffer, 5 μl (∼50 units) of restriction enzyme HindIII, and 85 μl of H2O, and the reaction was incubated at 37° C. for two hours. After the HindIII digestion, the DNA was precipitated, and the DNA pellet was dissolved in 10 μl of 10X SalI reaction buffer (1.5 M NaCl; 60 mM Tris-HCl, pH=7.9; 60 mM MgCl2; 60 mM 2-mercaptoethanol; and 1 mg/ml BSA), 5 μl (~50 units) of restriction enzyme SalI, and 85 μl of H₂O. The resulting SalI reaction mixture was incubated for 2 hours at 37° C. The HindIII-SalI-digested plasmid pSV2-HPC8 was loaded onto a 3.5% polyacrylamide gel and electrophoresed until the desired ~0.29 kb HindIII-SalI restriction fragment was separated from the other reaction products. The desired fragment was isolated from the gel; about 2 μg of the fragment were obtained and suspended in 10 μl of TE buffer.

Fifty μg of plasmid pSV2-HPC8 were dissolved in 10 μl of 10X BglII reaction buffer, 5 μl (50 units) of restriction enzyme BglII, and 85 μl of H₂O, and the reaction was incubated at 37° C. for two hours. After the BglII digestion, the DNA was precipitated, and the DNA pellet was dissolved in 10 μl of 10X SalI reaction buffer, 5 μl (~50 units) of restriction enzyme SalI, and 85 μl of H₂O. The resulting SalI reaction mixture was incubated for 2 hours at 37° C. The SalI-BglII-digested plasmid pSV2-HPC8 was loaded onto a 3.5% polyacrylamide gel and electrophoresed until the desired ~1.15 kb SalI-BglII restriction fragment was separated from the other reaction products. The ~1.15 kb SalI-BglII restriction fragment was isolated from the gel; about 8 μg of fragment were obtained and suspended in 10 μl of TE buffer.

Approximately 10 μg of plasmid pSV2-β-globin DNA (NRRL B—15928) were dissolved in 10 μl of 10X HindIII reaction buffer, 5 μl (~50 units) of restriction enzyme HindIII, and 85 μl of H₂O, and the reaction was placed at 37° C. for 2 hours. The reaction mixture was then made 0.25 M in NaOAc, and after the addition of two volumes of ethanol and incubation in a dry ice-ethanol bath, the DNA was pelleted by centrifugation. The HindIII-digested plasmid pSV2-β-globin was dissolved in 10 μl of 10X BglII buffer, 5 μl (~50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The desired ~4.2 kb HindIII-BglII restriction fragment was isolated from the gel; about 5 μg of the desired fragment were obtained and suspended in 10 μl of TE buffer.

Two μl of the ~0.29 kb HindIII-SalI fragment of plasmid pSV2-HPC8, 2 μl of the ~1.15 kb SalI-BglII fragment of plasmid pSV2-HPC8, and 2 μl of the ~4.2 kb HindIII-BglII fragment of plasmid pSV2-β-globin were mixed together and ligated with T4 DNA ligase. The ligated DNA constituted the desired plasmid pL133; a restriction site and function map of plasmid pL133 is presented in FIG. 2 of the accompanying drawings. The ligated DNA was used to transform *E. coli* K12 RR1, and the desired *E. coli* K12 RR1/pL133 transformants were identified by their ampicillin-resistant phenotype and by restriction enzyme analysis of their plasmid DNA.

F. Construction of Plasmid pLPC From Plasmids pL133 and pBLcat

About 20 μg of plasmid pBLcat DNA were dissolved in 10 μl of 10X HindIII buffer and 80 μl of H₂O. About 10 μl (~100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ~0.87 kb HindIII restriction fragment that comprises the BK enhancer and Ad2 late promoter was separated from the other digestion products; then, the ~0.87 kb fragment was isolated, purified, and prepared for ligation. About 2 μg of the desired fragment were obtained and dissolved in 5 μl of TE buffer.

About 1.5 μg of plasmid pL133 DNA were dissolved in 2 μl of 10X HindIII buffer and 16 μl of H₂O. About 1 μl (~10 units) of restriction enzyme HindIII was added to the solution of DNA, and the resulting reaction was incubated at 37° C. for 2 hours. The DNA was then diluted to 100 μl with TE buffer and treated with ~0.06 units of calf-intestinal alkaline phosphatase, and the resulting reaction was incubated at 37° C. for 30 minutes. The solution was adjusted to contain 1X SET (5 mM Tris-HCl, pH=7.8; 5 mM EDTA; and 150 mM NaCl), 0.3M NaOAc, and 0.5% SDS and then incubated at 65° C. for 45 minutes. The HindIII-digested plasmid pL133 DNA was then extracted twice with phenol and once with chloroform, precipitated with ethanol, and resuspended in 10 μl of TE buffer.

About 5 μl of the ~0.87 kb HindIII restriction fragment of plasmid pBLcat were added to the 1.5 μg (10 μl) of HindIII-digested plasmid pL133, and then, 2 μl of 10X ligase buffer, 1 μl (~10 units) of T4 DNA ligase, and 2 μl of H₂O were added to the solution of DNA, and the resulting reaction was incubated at 16° C. overnight. The ligated DNA constituted the desired plasmid pLPC.

The ligated DNA was used to transform *E. coli* K12 HB101 in substantial accordance with the procedure of Example 2B. The transformed cells were plated on L-agar plates containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only one of which yields plasmid pLPC. A restriction site and function map of plasmid pLPC is presented in FIG. 1, Part D, of the accompanying drawings.

EXAMPLE 3

The Construction of Plasmid pLAPC-IRS

Plasmid pLAPC-IRS was constructed in substantial accordance with the site-specific mutagenesis and other construction protocols used in the construction of plasmid pLAPC, as described in Example 1. Buffers and annealing conditions used in the construction of plasmid pLAPC-IRS, however, were as described by Zoller and Smith, 1984, DNA 3:479–489.

In the construction of plasmid pLAPC-IRS, phage M13mp18-HE1 (see Example 1B) were subjected to site-specific mutagenesis using the mutagenizing oligonucleotide depicted below:
5'-CGCAGTCACCTGAAACGACCCCGCC-CCAGCCGCAAGCGGCGCCTCATTGATG-GGAAGATG- 3'.

The mutagenized phage resulting from the site-specific mutagenesis were designated M13mp18-HE3.

Final construction of plasmid pLAPC.IRS proceeded in a manner analogous to the construction of plasmid pLAPC, set forth in Example 1C. However, plasmid pLAPC was constructed using two restriction fragments originating from plasmid pLPC. In the construction of plasmid pLAPC-IRS, these same two fragments were instead obtained from plasmid pLAPC. The reason for using plasmid pLAPC as the source of the fragments, instead of plasmid pLPC, was to facilitate restriction analysis in identifying the plasmid pLAPC-IRS transformants. Because plasmids pLPC and pLAPC-IRS are very close to the same size, it would have been difficult to distinguish "parentals" (plasmid pLPC) from plasmid pLAPC-IRS. However, because plasmid pLAPC is smaller than plasmid pLAPC-IRS, by obtaining the two fragments from plasmid pLAPC, one could readily distinguish parentals (plasmid pLAPC) from the desired plasmid pLAPC-IRS. Thus, to construct plasmid pLAPC-IRS, the ~0.7 kb SstI-SalI restriction fragment of phage M13mp18-HE3 was ligated to the ~3.76 kb EcoRI-SalI restriction fragment of plasmid pLAPC and the ~2.0 kb EcoRI-SstI restriction fragment of plasmid pLAPC. The ligated DNA constituted the desired plasmid pLAPC-IRS, which was transformed into E. coli K12 RV308. The resulting E. coli K12 RV308/pLAPC-IRS transformants were used to obtain a large-scale preparation of plasmid pLAPC-IRS DNA for use in transformations of eukaryotic cells.

EXAMPLE 4

Construction of Adenovirus-transformed Human Embryonic Kidney Cell Line 293/pLAPC-IRS and Adenovirus-transformed Syrian Hamster Cell Line AV12/pLAPC-IRS Transformants Human Embryonic Kidney Cell Line 293 is available from the American Type Culture Collection under the accession number ATCC CRL 1573. The adenovirus-transformed Syrian hamster cell line AV12 is also available from the American Type Culture Collection under the accession number ATCC CRL 9595. The transformation procedure described below refers to 293 cells as the host cell line; however, the procedure is generally applicable to most eukaryotic cell lines, including the AV12 cell line, and to the expression vectors of the invention.

293 cells are obtained from the ATCC under the accession number CRL 1573 in a 25 mm$^2$ flask containing a confluent monolayer of about $5.5 \times 10^6$ cells in Eagle's Minimum Essential Medium (Gibco) with 10% heat-inactivated horse serum. The flask is incubated at 37° C.; medium is changed twice weekly. Media is composed of DMEM (Gibco) supplemented with 10% fetal calf serum, 50 μg/ml gentamicin, and 10 μg/ml AquaMEPHYTON® phytonadione vitamin $K_1$ (Merck Sharp and Dohme, Merck and Co., Inc., West Point, PA 19486). The cells are subcultured by removing the medium, rinsing with Hank's Balanced Salts solution (Gibco), adding 0.25% trypsin (containing 0.2 g/L EDTA) for 1-2 minutes, rinsing with fresh medium, aspirating, and dispensing into new flasks at a subcultivation ratio of 1:5 or 1:10.

One day prior to transformation, cells are seeded at $0.7 \times 10^6$ cells per 100 mm dish. Sterile, ethanol-precipitated plasmid DNA dissolved in TE buffer is used to prepare a 2X DNA-CaCl$_2$ solution containing 25 μg/ml of the transforming plasmid DNA (for plasmid pLAPC-IRS transformations, usually two plasmids are used, plasmid pLAPC-IRS and a plasmid that contains a selectable marker, as discussed below) and 250 mM CaCl$_2$. 2X HBSS is prepared containing 280 mM NaCl, 50 mM Hepes, and 1.5 mM sodium phosphate, with the pH adjusted to 7.05-7.15. The 2X DNA-CaCl$_2$ solution is added dropwise to an equal volume of sterile 2X HBSS. A one ml sterile plastic pipette with a cotton plug is inserted into the mixing tube that contains the 2X HBSS, and bubbles are introduced by blowing while the DNA is being added. The calcium-phosphate-DNA precipitate is allowed to form without agitation for 30-45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the media is replaced with fresh media and the cells allowed to incubate for an additional 72 hours before providing selective pressure. For plasmids that do not comprise a selectable marker that functions in eukaryotic cells, such as plasmid pLAPC-IRS, the transformation procedure utilizes a mixture of plasmids: the expression vector of the present invention that lacks a selectable marker; and an expression vector that comprises a selectable marker that functions in eukaryotic cells. A variety of vectors are available for use in such cotransformation systems and include plasmids pSV2-dhfr (ATCC 37146), pSV2-neo (ATCC 37149), pSV2-gpt (ATCC 37145), and pSV2-hyg (NRRL B—18039). Plasmid pSV2-hyg confers resistance to hygromycin B to eukaryotic host cells. This co-transformation technique allows for the selection of cells that contain the plasmid with the selectable marker. These cells are further examined to identify cells that comprise both of the transforming plasmids. Of course, the present invention also comprises expression vectors that contain a selectable marker for eukaryotic cells and thus do not require use of the cotransformation technique.

For cells transfected with plasmids containing the hygromycin resistance-conferring gene, hygromycin B is added to the growth medium to a final concentration of about 200 μg/ml. The cells are then incubated at 37° C. for 2-4 weeks with medium changes at 3 to 4 day intervals. The resulting hygromycin-resistant colonies are transferred to individual culture flasks for characterization. Plasmid pSV2-neo confers resistance to neomycin (G418 is also used in place of neomycin), and selection of neomycin-resistant colonies is performed in substantial accordance with the selection procedure for hygromycin-resistant cells, except that G418 is added to a final concentration of 400 μg/ml.

The use of the dihydrofolate reductase (dhfr) gene or the methotrexate resistance-conferring derivative of the dhfr gene (dhfr-mtx) as a selectable marker for introducing a gene or plasmid into a dhfr-deficient cell line and the subsequent use of methotrexate to amplify the copy number of the plasmid has been well established in the literature. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype. Although the use of dhfr as a selectable and amplifiable marker in dhfr-producing cells has not been well studied, evidence in the literature would suggest that dhfr can be used as a selectable marker and for gene amplification in dhfr-producing cells. The present invention is not limited by the selectable marker used on expression vectors. Moreover, amplifiable markers such as metallothionein genes, adenosine deaminase genes, or members of the multigene resistance family, exemplified by the P-glycoprotein gene, can be utilized.

Transformation of the 293 and AV12 cell lines with a mixture of plasmid pLAPC-IRS and a hygromycin resistance-conferring vector and subsequent selection for hygromycin-resistant cells yielded a number of transformants. (Other transformants were obtained by using plasmid pSV2-neo as the cotransforming vector and selecting for G418-resistant cells.) These transformants are analyzed, as described in Example 5, to determine which hygromycin-resistant cells contained plasmid pLAPC-IRS.

EXAMPLE 5

The hygromycin-resistant transformants obtained in Example 4 are grown on 100 mm² tissue culture dishes at a density of several hundred cell clones per tissue culture dish. The media is decanted, and the cells are rinsed twice with 5 ml aliquots of Hank's Balanced salt solution (Gibco). A solution of sterile 0.45% agar (Sigma Type 4 agarose, catalogue #A3643, Sigma Chemical Co., P.O. Box 14508, St. Louis, MO 63178) is prepared by mixing 1 ml of 1.8% agar (47° C.) with 3 ml of Dulbecco's Modified Eagle's (DME) Salts (Gibco) (37° C.), and 2 ml of this 0.45% agar solution are layered over the cells.

Nitrocellulose filters (Schleicher and Schuell, Inc., Keene, NH 03431) are boiled and then autoclaved 2 hours to remove the wetting agent, which is toxic to the cells. The filters are then placed on top of the agar layer, and after air bubbles are removed, the plates are incubated at 37° C. for 1 to 3 hours. The filters, previously marked to indicate the original orientation of the filter on the dish so as to facilitate later identification of colonies, are then removed and placed in PBS (50 mM Tris-HCl, pH=7.2, and 150 mM NaCl).

To keep the cells on the dish viable during analysis of the filters, the cells are overlayed with 8 ml of a mixture containing 2 ml of 1.8% agar (47° C.), 2 ml of DME salts (37° C.), and 4 ml of DME salts with 20% fetal bovine serum (37° C.). The cells are then placed in a 37° C. incubator.

All washes and reactions carried out on the filters are accomplished while the filters are on a rocking platform. The filters are first blocked by incubation at room temperature in 5% milk in PBS. The filters are then rinsed (5 minutes/rinse) four times in PBS. A 10 μg/ml biotinylated goat anti-human protein C polyclonal antibody in 2.5% bovine serum albumin is added to the filter (in sufficient quantities to cover the filter), which is then incubated at 37° C. for 1 hour.

Purification of protein C, for subsequent use to prepare antibody against protein C, can be accomplished as described by Kisiel, 1979, J. Clin. Invest. 64:761. Polyclonal antibody can be prepared by the procedure disclosed in *Structural Concepts in Immunology and Immunochemistry* by E. A. Kabat, published in 1968 by Hold, Rhinehart, and Winston. Monoclonal antibody, which is also suitable for use in the assay, can be prepared as disclosed in Kohler and Milstein, 1975, Nature, 256:495, or as disclosed in U.S. Pat. No. 4,696,895; EPO Pub. No. 205046; Laurell et al., 1985, FEBS 191(1):75; Suzuki et al., 1985, J. Biochem. 97:127-138; and EPO Pub. No. 138222. The avidin D and biotinylated horse radish peroxidase (HRP) used in the assay are obtained in a Vectastain ™ kit (Vector Laboratories, Inc., 30 Ingold Road, Burlingame, CA 4010). Biotin is also obtained from Vector Laboratories, Inc.

The filters are rinsed four times with PBS at 4° C. Then, avidin D and biotinylated horse radish peroxidase are prepared and added as per the manufacturer's instructions in the Vectastain ™ (Vector Laboratories) kit. The filters are incubated with the HRP-conjugated avidin D for 1 hour at 4° C. (longer incubation times, i.e., overnight, can be used when small amounts of protein are being secreted); then, the filters are rinsed four times with PBS at 4° C.

To develop the indicator color on the filters, about 30 mg of HRP color-development reagent (4-chloro1-napthol, Sigma) dissolved in ice-cold 100% methanol are added to 50 ml of PBS and 30 μl of 30% $H_2O_2$. This mixture is added to the nitrocellulose filters, which are incubated at room temperature until the color develops. Colonies secreting the most human protein C will be indicated on the filters not only by earliest appearance of the color but also by darker spots on the filter.

After the filters have been developed, the filters are again realigned with the original plates to determine which colonies are associated with which spots on the filter. The colonies secreting the most human protein C are then selected and used for production of activated human protein C.

Those skilled in the art will recognize that the above assay is merely illustrative of the method of identifying high secreting cell lines. A variety of assay procedures can be successfully employed in the method. For instance, a double-antibody reaction can be employed in which the biotinylated goat anti protein C antibody is replaced with a goat anti-protein C antibody (IgG) and a biotinylated anti-goat IgG antibody. The method can be successfully employed with any secreted protein from any cell.

We claim:

1. A DNA compound comprising a coding sequence for a protein, said protein comprising, from the amino-terminus to the carboxy-terminus:
   (a) a signal peptide and propeptide of a γ-carboxylated, secreted protein;
   (b) the light chain of human protein C;
   (c) a dipeptide selected from lysine-arginine, lysine-lysine, and arginine-arginine;
   (d) a cleavage sequence for a cell associated protease, said cleavage sequence containing a dibasic dipeptide at the C-terminus; and
   (e) the activated heavy chain of human protein C.

2. The DNA compound of claim 1, wherein said cleavage sequence is an amino acid residue sequence selected from the group consisting of PRPSRKRR, KKRSHLKR, QTLERRKR, LEGSLQKR, FYTPKTRR, MLVQGSWQ, QVLRIRKR, KILNRPKR, NILARVTR, ARFRRGAR, DQMNEDKR, QWLMNTKR, NRDDIAKR, LVKGRGRR, AND IVEELGRR, wherein F is Phenylalanine, L is Leucine, I is Isoleucine, M is Methionine, V is Valine, S is Serine, P is Proline, T is Threonine, A is Alanine, Y is Tyrosine, H is Histidine, Q is Glutamine, N is Asparagine, K is Lysine, D is Aspartic Acid, E is Glutamic Acid, W is Tryptophan, R is Arginine, and G is Glycine.

3. The DNA compound of claim 2, wherein said signal peptide and propeptide are the signal peptide and propeptide of nascent human protein C.

4. The DNA compound of claim 3, wherein said cleavage sequence is PRPSRKRR.

5. The DNA compound of claim 4, wherein the polypeptide encoded by said DNA is:

```
H2N—  MET TRP GLN LEU THR SER LEU LEU LEU PHE VAL ALA THR GLY ILE
       SER GLY THR PRO ALA PRO LEU ASP SER VAL PHE SER SER SER GLU ARG
       ALA HIS GLN VAL LEU ARG ILE ARG LYS ARG ALA ASN SER PHE LEU GLU
       GLU LEU ARG HIS SER SER LEU GLU ARG GLU CYS ILE GLU GLU ILE CYS
       ASP PHE GLU GLU ALA LYS GLU ILE PHE GLN ASN VAL ASP ASP THR LEU
       ALA PHE TRP SER LYS HIS VAL ASP GLY ASP GLN CYS LEU VAL LEU PRO
       LEU GLU HIS PRO CYS ALA SER LEU CYS CYS GLY HIS GLY THR CYS ILE
       ASP GLY ILE GLY SER PHE SER CYS ASP CYS ARG SER GLY TRP GLU GLY
       ARG PHE CYS GLN ARG GLU VAL SER PHE LEU ASN CYS SER LEU ASP ASN
       GLY GLY CYS THR HIS TYR CYS LEU GLU GLU VAL GLY TRP ARG ARG CYS
       SER CYS ALA PRO GLY TYR LYS LEU GLY ASP ASP LEU LEU GLN CYS HIS
       PRO ALA VAL LYS PHE PRO CYS GLY ARG PRO TRP LYS ARG MET GLU LYS
       LYS ARG SER HIS LEU LYS ARG PRO ARG PRO SER ARG LYS ARG ARG LEU
       ILE ASP GLY LYS MET THR ARG ARG GLY ASP SER PRO TRP GLN VAL VAL
       LEU LEU ASP SER LYS LYS LYS LEU ALA CYS GLY ALA VAL LEU ILE HIS
       PRO SER TRP VAL LEU THR ALA ALA HIS CYS MET ASP GLU SER LYS LYS
       LEU LEU VAL ARG LEU GLY GLU TYR ASP LEU ARG ARG TRP GLU LYS TRP
       GLU LEU ASP LEU ASP ILE LYS GLU VAL PHE VAL HIS PRO ASN TYR SER
       LYS SER THR THR ASP ASN ASP ILE ALA LEU LEU HIS LEU ALA GLN PRO
       ALA THR LEU SER GLN THR ILE VAL PRO ILE CYS LEU PRO ASP SER GLY
       LEU ALA GLU ARG GLU LEU ASN GLN ALA GLY GLN GLU THR LEU VAL THR
       GLY TRP GLY TYR HIS SER SER ARG GLU LYS GLU ALA LYS ARG ASN ARG
       THR PHE VAL LEU ASN PHE ILE LYS ILE PRO VAL VAL PRO HIS ASN GLU
       CYS SER GLU VAL MET SER ASN MET VAL SER GLU ASN MET LEU CYS ALA
       GLY ILE LEU GLY ASP ARG GLN ASP ALA CYS GLU GLY ASP SER GLY GLY
       PRO MET VAL ALA SER PHE HIS GLY THR TRP PHE LEU VAL GLY LEU VAL
       SER TRP GLY GLU GLY CYS GLY LEU LEU HIS ASN TYR GLY VAL TYR THR
       LYS VAL SER ARG TYR LEU ASP TRP ILE HIS GLY HIS ILE ARG ASP LYS
       GLU ALA PRO GLN LYS SER TRP ALA PRO—COOH
``` wherein ALA is Alanine, ARG is Arginine, ASN is Asparagine, ASP is Aspartic acid, —COOH is the carboxyterminus, CYS is Cysteine, GLN is Glutamine, GLU is Glutamic Acid, GLY is Glycine, H2N— is the aminoterminus, HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

6. A recombinant DNA expression vector comprising the DNA compound of claim 5.

7. The vector of claim 6 that is plasmid pLAPC-IRS.

8. A eukaryotic host cell transformed with a vector of claim 6.

9. The eukaryotic host cell of claim 8 that is 293/pLAPC-IRS.

10. The eukaryotic host cell of claim 8 that is AV12/-pLAPC-IRS.

11. A method for producing recombinant activated protein C directly upon secretion from a eukaryotic host cell, which comprises
(A) transforming a host cell with a recombinant DNA vector, said vector comprising:
 (i) a DNA sequence that encodes an amino acid residue sequence, said amino acid residue sequence comprising, from the amino-terminus to the carboxy-terminus:
  (a) a signal peptide and a propeptide of a γ-carboxylated, secreted protein;
  (b) the light chain of human protein C;
  (c) a dipeptide selected from lysine-argine, lysine-lysine, and arginine-arginine;
  (d) a cleavage sequence for a cell associated protease, said cleavage sequence containing a dibasic dipeptide at the C-terminus; and
  (e) the activated heavy chain of human protein C; and
 (ii) a promoter positioned to drive expression of said DNA sequence; and
(B) culturing said host cell transformed in step (A) under conditions such that said amino acid residue sequence is produced.

12. The method of claim 11, wherein said cleavage sequence is selected from the group consisting of PRPSRKRR, KKRSHLKR, QTLERRKR, LEGSLQKR, FYTPKTRR, MLVQGSWQ, QVLRIRKR, KILNRPKR, NILARVTR, ARFRRGAR, DQMNEDKR, QWLMNTKR, NRDDIAKR, LVKGRGRR, AND IVEELGRR, wherein F is phenylalanine, L is Leucine, I is Isoleucine, M is Methionine, V is Valine, S is Serine, P is Proline, T is Threonine, A is Alanine, Y is Tyrosine, H is Histidine, Q is Glutamine, N is Asparagine, K is Lysine, D is Aspartic Acid, E is Glutamic Acid, W is Tryptophan, R is Arginine, and G is Glycine.

13. The method of claim 12, wherein said cleavage sequence is PRPSRKRR.

14. The method of claim 13, wherein said DNA sequence encodes the amino acid residue sequence

```
H2N—  MET TRP GLN LEU THR SER LEU LEU LEU PHE VAL ALA THR TRP GLY ILE
       SER GLY THR PRO ALA PRO LEU ASP SER VAL PHE SER SER SER GLU ARG
       ALA HIS GLN VAL LEU ARG ILE ARG LYS ARG ALA ASN SER PHE LEU GLU
       GLU LEU ARG HIS SER SER LEU GLU ARG GLU CYS ILE GLU GLU ILE CYS
       ASP PHE GLU GLU ALA LYS GLU ILE PHE GLN ASN VAL ASP ASP THR LEU
       ALA PHE TRP SER LYS HIS VAL ASP GLY ASP GLN CYS LEU VAL LEU PRO
       LEU GLU HIS PRO CYS ALA SER LEU CYS CYS GLY HIS GLY THR CYS ILE
       ASP GLY ILE GLY SER PHE SER CYS ASP CYS ARG SER GLY TRP GLU GLY
       ARG PHE CYS GLN ARG GLU VAL SER PHE LEU ASN CYS SER LEU ASP ASN
       GLY GLY CYS THR HIS TYR CYS LEU GLU GLU VAL GLY TRP ARG ARG CYS
       SER CYS ALA PRO GLY TYR LYS LEU GLY ASP ASP LEU LEU GLN CYS HIS
       PRO ALA VAL LYS PHE PRO CYS GLY ARG PRO TRP LYS ARG MET GLU LYS
```

-continued

```
LYS ARG SER HIS LEU LYS ARG PRO ARG PRO SET ARG LYS ARG ARG LEU
ILE ASP GLY LYS MET THR ARG ARG GLY ASP SER PRO TRP GLN VAL VAL
LEU LEU ASP SER LYS LYS LYS LEU ALA CYS GLY ALA VAL LEU ILE HIS
PRO SER TRP VAL LEU THR ALA ALA HIS CYS MET ASP GLU SER LYS LYS
LEU LEU VAL ARG LEU GLY GLU TYR ASP LEU ARG ARG TRP GLU LYS TRP
GLU LEU ASP LEU ASP ILE LYS GLU VAL PHE VAL HIS PRO ASN TYR SER
LYS SER THR THR ASP ASN ASP ILE ALA LEU LEU HIS LEU ALA GLN PRO
ALA THR LEU SER GLN THR ILE VAL PRO ILE CYS LEU PRO ASP SER GLY
LEU ALA GLU ARG GLU LEU ASN GLN ALA GLY GLN GLU THR LEU VAL THR
GLY TRP GLY TYR HIS SER SER ARG GLU LYS GLU ALA LYS ARG ASN ARG
THR PHE VAL LEU ASN PHE ILE LYS ILE PRO VAL VAL PRO HIS ASN GLU
CYS SER GLU VAL MET SER ASN MET VAL SER GLU ASN MET LEU CYS ALA
GLY ILE LEU GLY ASP ARG GLN ASP ALA CYS GLU GLY ASP SER GLY GLY
PRO MET VAL ALA SER PHE HIS GLY THR TRP PHE LEU VAL GLY LEU VAL
SER TRP GLY GLU GLY CYS GLY LEU LEU HIS ASN TYR GLY VAL TYR THR
LYS VAL SER ARG TYR LEU ASP TRP ILE HIS GLY HIS ILE ARG ASP LYS
GLU ALA PRO GLN LYS SER TRP ALA PRO—COOH
``` wherein ALA is Alanine, ARG is Arginine, ASN is Asparagine, ASP is Aspartic acid, —COOH is the carboxy-terminus, CYS is cysteine, GLN is Glutamine, GLU is Glutamic Acid, GLY is Glycine, H₂N— is the amino-terminus HIS is Histidine, ILE is Isoleucine, LEU is Leucine, LYS is Lysine, MET is Methionine, PHE is Phenylalanine, PRO is Proline, SER is Serine, THR is Threonine, TRP is Tryptophan, TYR is Tyrosine, and VAL is Valine.

15. The method of claim 14, wherein said host cell is selected from the group consisting of 293 and AV12 host cells.

16. The method of claim 15, wherein said host cell cultured in step (B) is selected from the group consisting of 293/pLAPC-IRS and AV12/pLAPC-IRS host cells.

17. A vector selected from the group consisting of vectors pLAPC, M13mp18HE1, M13mp18HE2, and M13mp18HE3.

* * * * *